(12) United States Patent
Marczak et al.

(10) Patent No.: US 10,669,572 B2
(45) Date of Patent: Jun. 2, 2020

(54) ULTRA-SENSITIVE MULTI-TARGET LATERAL FLOW MOLECULAR ASSAY WITH FIELD-INDUCED PRECIPITATION

(71) Applicant: University of Notre Dame du Lac, Notre Dame, IN (US)

(72) Inventors: Steve Marczak, South Bend, IN (US); Hsueh-Chia Chang, Granger, IN (US); Zdenek Slouka, Prague (CI); Satyajyoti Senapati, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 257 days.

(21) Appl. No.: 15/994,546

(22) Filed: May 31, 2018

(65) Prior Publication Data

US 2018/0346975 A1  Dec. 6, 2018

Related U.S. Application Data

(60) Provisional application No. 62/513,142, filed on May 31, 2017.

(51) Int. Cl.
*G01N 27/447* (2006.01)
*C12Q 1/6832* (2018.01)
(Continued)

(52) U.S. Cl.
CPC ........... *C12Q 1/6832* (2013.01); *C12N 15/10* (2013.01); *C12Q 1/6806* (2013.01);
(Continued)

(58) Field of Classification Search
CPC .... C12Q 1/6832; C12Q 1/6806; C12N 15/10; C12N 15/1017; C12N 15/101; C12N 15/1006; G01N 1/4005; G01N 27/44721; G01N 27/44791; G01N 2001/4038; G01N 2001/4011
See application file for complete search history.

(56) References Cited

U.S. PATENT DOCUMENTS 7,651,600 B2   2/2010   Stratten
7,828,948 B1  11/2010   Hatch et al.
(Continued)

FOREIGN PATENT DOCUMENTS

DE   19613867 C1   7/1997
GB    2506630 A    4/2014
(Continued)

OTHER PUBLICATIONS

A. Persat and J.G. Santiago ("MicroRNA Profiling by Simultaneous Selective Isotachophoresis and Hybridization with Molecular Becons", Analytical Chemistry, 83(6): p. 2310-2316, Mar. (Year: 2011).*
(Continued)

*Primary Examiner* — J. Christopher Ball
(74) *Attorney, Agent, or Firm* — Michael Best & Friedrich LLP

(57) ABSTRACT

Described are methods for detecting and quantifying biomolecules such as polynucleotides or polypeptides in an electrophoresis matrix using ion concentration polarization and nanoparticle aggregation.

29 Claims, 16 Drawing Sheets

Figure 2A:
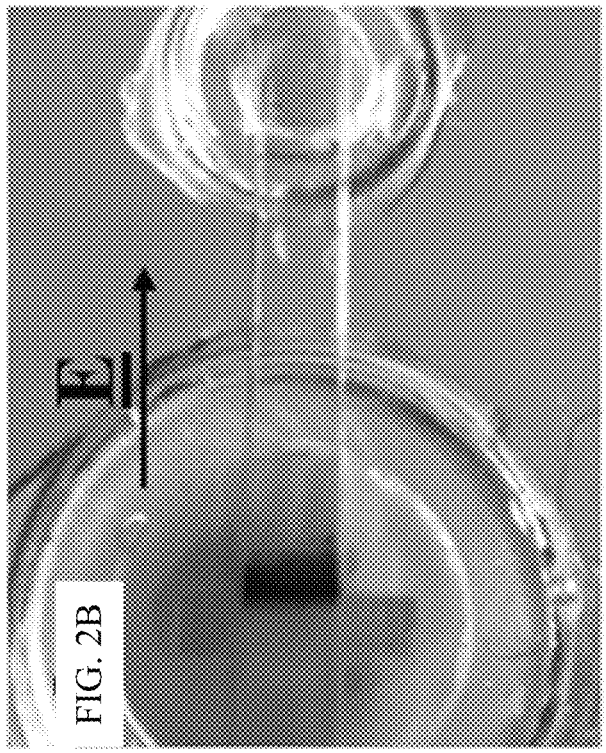

Specification includes a Sequence Listing.

(51) Int. Cl.
  *C12Q 1/6806*  (2018.01)
  *G01N 1/40*  (2006.01)
  *C12N 15/10*  (2006.01)
(52) U.S. Cl.
  CPC ..... *G01N 1/4005* (2013.01); *G01N 27/44721* (2013.01); *G01N 27/44791* (2013.01); *C12N 15/101* (2013.01); *C12N 15/1006* (2013.01); *C12N 15/1017* (2013.01); *G01N 2001/4011* (2013.01); *G01N 2001/4038* (2013.01)

(56) References Cited

U.S. PATENT DOCUMENTS

| | | | |
|---|---|---|---|
| 8,329,115 | B2 | 12/2012 | Han et al. |
| 9,575,031 | B2 | 2/2017 | Vulto et al. |
| 9,845,252 | B2 | 12/2017 | Kwak et al. |
| 9,850,146 | B2 | 12/2017 | Choi et al. |
| 2005/0284762 | A1 | 12/2005 | Astorga-Wells et al. |
| 2006/0180469 | A1 | 8/2006 | Han et al. |
| 2007/0088335 | A1 | 4/2007 | Jolly |
| 2009/0120796 | A1 | 5/2009 | Han et al. |
| 2009/0242406 | A1 | 10/2009 | Han et al. |
| 2010/0252435 | A1 | 10/2010 | Weber |
| 2011/0198225 | A1 | 8/2011 | Kim et al. |
| 2011/0220498 | A1 | 9/2011 | Ko et al. |
| 2013/0068632 | A1 | 3/2013 | Chang et al. |
| 2015/0119280 | A1 | 4/2015 | Srinivas et al. |
| 2016/0023925 | A1 | 1/2016 | Liu |
| 2016/0115045 | A1 | 4/2016 | Kim et al. |
| 2016/0199853 | A1 | 7/2016 | Harwood et al. |

FOREIGN PATENT DOCUMENTS

| | | | |
|---|---|---|---|
| KR | 20150094955 | A | 8/2015 |
| KR | 20160037871 | A | 4/2016 |
| KR | 101749600 | B1 | 6/2017 |
| KR | 101769529 | B1 | 8/2017 |
| KR | 20170106202 | A | 9/2017 |
| WO | WO 2017/155298 | A2 | 9/2017 |

OTHER PUBLICATIONS

Arcaro et al., "Differential expression of cancer-related proteins in paired breast milk samples from women with breast cancer," J. Hum. Lact., 2012, 28, 543-546.
Brown et al., "Seeding of Colloidal Au Nanoparticle Solutions. 2. Improved Control of Particle Size and Shape," J. Chem. Mater., 2000, 12, 306-313.
Cao et al., "A label-free fluorescent molecular beacon based on DNA-Ag nanoclusters for the construction of versatile Biosensors," Biosensors & Bioelectronics, 2015, 74, 318-321.
Capello et al., "Sequential Validation of Blood-Based Protein Biomarker Candidates for Early-Stage Pancreatic Cancer," J. Natl. Cancer Inst., 2017, 109, djw266, 9 pages.
Chang et al., "Nanoscale Electrokinetics and Microvortices: How Microhydrodynamics Affects Nanofluidic Ion Flux," Annual Review of Fluid Mechanics, 2012, 44, 401-426.
Chen et al., "BEAMing and Droplet Digital PCR Analysis of Mutant IDH1 mRNA in Glioma Patient Serum and Cerebrospinal Fluid Extracellular Vesicles," Mol. Ther. Nucleic Acids, 2013, 2, e109, 10 pages.
Chen et al., "Microfluidic isolation and transcriptome analysis of serum microvesicles," Lab Chip, 2010, 10, 505-511.
Cheng et al., "A rapid field-use assay for mismatch number and location of hybridized DNAs," Lab Chip, 2010, 10, 828-831.
Chevillet et al., "Quantitative and stoichiometric analysis of the microRNA content of exosomes," PNAS, 2014, 111, 14888-14893.
Cho et al., "Isolation of extracellular vesicle from blood plasma using electrophoretic migration through porous membrane," Sensors and Actuators B Chemical, 2016, 233, 289-297.
Choi et al., "Extracellular vesicles shed from gefitinib-resistant nonsmall cell lung cancer regulate the tumor microenvironment," Proteomics, 2014, 14, 1845-1856.
Chua et al., "A rapid DNA biosensor for the molecular diagnosis of infectious disease," Biosensors & Bioelectronics, 2011, 26, 3825-3831.
Clayton et al., "Analysis of antigen presenting cell derived exosomes, based on immuno-magnetic isolation and flow cytometry," J. Immunol. Methods, 2001, 247, 163-174.
Corstjens et al., "Lateral-flow and up-converting phosphor reporters to detect single-stranded nucleic acids in a sandwich-hybridization assay," Anal. Biochem., 2003, 312, 191-200.
Davies et al., "Microfluidic filtration system to isolate extracellular vesicles from blood," Lab Chip, 2012, 12, 5202-5210.
De Avila et al., "Determinants of the Detection Limit and Specificity of Surface-Based Biosensors," Anal. Chem., 2013, 85 (14), 6593-6597.
Debernardi et al., "Noninvasive urinary miRNA biomarkers for early detection of pancreatic adenocarcinoma," Am. J. Cancer Res., 2015, 5, 3455-3466.
Del Boccio et al., "A hyphenated microLC-Q-TOF-MS platform for exosomal lipidomics investigations: application to RCC urinary exosomes," Electrophoresis, 2012, 33, 689-696.
Demers et al., "A fluorescence-based method for determining the surface coverage and hybridization efficiency of thiol-capped oligonucleotides bound to gold thin films and nanoparticles," Anal. Chem., 2000, 72, 5535-5541.
Egatz-Gomez et al., "Future microfluidic and nanofluidic modular platforms for nucleic acid liquid biopsy in precision medicine," Biomicrofluidics, 2016, 10, 032902, 27 pages.
Elghanian et al., "Selective colorimetric detection of polynucleotides based on the distance-dependent optical properties of gold nanoparticles," Science, 1997, 277 (5329), 1078-1081.
Fang et al., "A lateral flow biosensor for rapid detection of DNA-binding protein c-jun," Biosensors & Bioelectronics, 2011, 27, 192-196.
Gagnon et al., "Dielectrophoretic detection and quantification of hybridized DNA molecules on nano-genetic particles," Electrophoresis, 2008, 29, 4808-4812.
Gallo et al., "The Majority of MicroRNAs Detectable in Serum and Saliva Is Concentrated in Exosomes," PLoS One, 2012, 7, 30679, 5 pages.
Gao et al., "Visual Detection of microRNA with Lateral Flow Nucleic Acid Biosensor," Biosensors & Bioelectronics, 2014, 54, 578-584.
Garcia-Schwarz et al., "Integration of On-Chip Isotachophoresis and Functionalized Hydrogels for Enhanced-Sensitivity Nucleic Acid Detection," Anal. Chem., 2012, 84, 6366-6369.
Gong et al., "Direct DNA Analysis with Paper-Based Ion Concentration Polarization," J. Am. Chem. Soc., 2015, 137, 13913-13919.
Gong et al., "DNA surface hybridization regimes," PNAS USA, 2008, 105 (14), 5301-5306.
Grange et al., "Microvesicles Released from Human Renal Cancer Stem Cells Stimulate Angiogenesis and Formation of Lung Premetastatic Niche," Tumor Stem Cell Biol., 2011, 71, 5346-5356.
Haiss et al., "Determination of Size and Concentration of Gold Nanoparticles from UV-Vis Spectra," Anal. Chem., 2007, 79, 4215-4221.
Hakulinen et al., "Secretion of active membrane type 1 matrix metalloproteinase (MMP-14) into extracellular space in microvesicular exosomes," J. Cell Biochem., 2008, 105, 1211-1218.
Hampl et al., "Upconverting phosphor reporters in immunochromatographic assays," Anal. Biochem., 2001, 288, 176-187.
Hanauer et al., "Separation of Nanoparticles by Gel Electrophoresis According to Size and Shape." Nano Letters, 2007, 7 (9), pp. 2881-2885.
Hao et al., "Circulating cell-free DNA in serum as a biomarker for diagnosis and prognostic prediction of colorectal cancer," Br. J.Cancer, 2014, 111, 1482-1489.
He et al., "Ultrasensitive nucleic acid biosensor based on enzyme-gold nanoparticle dual label and lateral flow strip biosensor," Biosensors & Bioelectronics, 2011, 26, 2018-2024.

(56) References Cited

OTHER PUBLICATIONS

Hermanson et al., "Dielectrophoretic assembly of electrically functional microwires from nanoparticle suspensions," Science, 2001, 294 (5544), 1082-1086.

Hlavacek et al., "Isotachophoretic purification of nanoparticles: Tuning optical properties of quantum dots," Electrophoresis, 2012, 33, 1427-1430.

Hlavacek et al., "Electrophoretic Characterization and Purification of Silica-Coated Photon-Upconverting Nanoparticles and Their Bioconjugates." Applied Materials & Interfaces, 2014, 6, pp. 6930-6935.

Hoshino et al., "Tumour exosome integrins determine organotropic metastasis," Nature, 2015, 527, 329-335.

Hou et al., "MicroRNA detection using lateral flow nucleic acid strips with gold nanoparticles," Talanta, 2012, 99, 375-379.

Hou et al., "Microfluidic integration of Western blotting is enabled by electrotransfer-assisted sodium dodecyl sulfate dilution," Analyst, 2013, 138, pp. 158-163.

Hu et al., "Oligonucleotide-linked gold nanoparticle aggregates for enhanced sensitivity in lateral flow assays," Lab Chip, 2013, 13, 4352-4357.

Javidi et al., "Cell-free microRNAs as cancer biomarkers: The odyssey of miRNAs through body fluids," Med. Oncol., 2014, 31, 295, 11 pages.

Jhaveri et al., "Isolation and Characterization of Trioxyethylene-Encapsulated Gold Nanoclusters Functionalized with a Single DNA Strand." Nano Letters, 2004, 4 (4), pp. 737-740.

Jia et al., "Highly sensitive electrochemical biosensor based on nonlinear hybridization chain reaction for DNA detection," Biosensors & Bioelectronics, 2016, 80, 392-397.

Kahlert et al., "Identification of double-stranded genomic DNA spanning all chromosomes with mutated KRAS and p53 DNA in the serum exosomes of patients with pancreatic cancer," J. Biol. Chem., 2014, 289, 3869-3875.

Keller et al., "Body fluid derived exosomes as a novel template for clinical diagnostics," J. Transl. Med. 2011, 9, 86, 9 pages.

Kim et al., "Electrophoretic separation of gold nanoparticles according to bifunctional molecules-induced charge and size." Electrophoresis, 2013, 34, pp. 911-916.

Kloepper et al., "Field-Induced Interfacial Properties of Gold Nanoparticles in AC Microelectrophoretic Experiments," J. Phys. Chem. B, 2004, 108, 2547-2553.

Koga et al., "Purification, characterization and biological significance of tumor-derived exosomes," Anticancer Res., 2005, 25, 3703-3708.

Lamparski et al., "Production and characterization of clinical grade exosomes derived from dendritic cells," J. Immunol. Methods, 2002, 270, 211-226.

Lee et al., "Acoustic Purification of Extracellular Microvesicles," ACS Nano, 2015, 9, 2321-2327.

Lee et al., "Oncogenic ras-driven cancer cell vesiculation leads to emission of double-stranded DNA capable of interacting with target cells," Biochem. Biophys. Res. Commun., 2014, 451, 295-301.

Levicky et al., "Physicochemical perspectives on DNA microarray and biosensor technologies," Trends Biotechnol., 2005, 23 (3), 143-149.

Li et al., "Analysis of the RNA content of the exosomes derived from blood serum and urine and its potential as biomarkers," Philos Trans. R. Soc. Lond. B Biol. Sci., 2014, 369, 20130502, 8 pages.

Li et al., "Enhanced electrochemical recognition of double-stranded DNA by using hybridization chain reaction and positively charged gold nanoparticles," Biosensors & Bioelectronics, 2015, 74, 687-690.

Li et al., "Exosomal microRNA-141 is upregulated in the serum of prostate cancer patients," Onco. Targets Ther., 2015, 9, 139-148.

Li et al., "Progress in Exosome Isolation Techniques," Theranostics, 2017, 7, 789-804.

Liu et al., "Adding sodium dodecylsulfate to the running electrolyte enhances the separation of gold nanoparticles by capillary electrophoresis," Anal. Chim. Acta, 2004, 510, 77-83.

Liu et al., "Analysis and applications of nanoparticles in the separation sciences: A case of gold nanoparticles," J. Chromatogr. A, 2009, 1216, 9034-9047.

Liu et al., "Plasmonic hotspots of dynamically assembled nanoparticles in nanocapillaries: Towards a micro ribonucleic acid profiling platform," Biomicrofluidics, 2013, 7, 061102, 4 pages.

Liu et al., "Studying the size/shape separation and optical properties of silver nanoparticles by capillary electrophoresis," J. Chromatogr. A, 2005, 1062, 139-145.

Lobb et al., "Optimized exosome isolation protocol for cell culture supernatant and human plasma," J. Extracell. Vesicles, 2015, 4, 27031, 11 pages.

Luga et al., "Exosomes mediate stromal mobilization of autocrine Wnt-PCP signaling in breast cancer cell migration," Cell, 2012, 151, 1542-1556.

Lujambio et al., "The microcosmos of cancer," Nature, 2012, 482, 347-355.

Luo et al., "Electrochemical DNA Sensor for Determination of p53 Tumor Suppressor Gene Incorporating Gold Nanoparticles Modification," Chin. J. Anal. Chem., 2013, 41 (11), 1664-1668.

Lv et al., "Exosomes mediate drug resistance transfer in MCF-7 breast cancer cells and a probable mechanism is delivery of P-glycoprotein," Tumor Biol., 2014, 35, 10773-10779.

Mao et al., "Disposable nucleic acid biosensors based on gold nanoparticle probes and lateral flow strip," Anal. Chem., 2009, 81, 1660-1668.

Marczak et al., "Induced nanoparticle aggregation for short nucleic acid quantification by depletion isotachophoresis," Biosensors and Bioelectronics, 2016, 86, 840-848.

Marczak et al., "Selectivity enhancements in gel-based DNA-nanoparticle assay by membrane-induced isotachophoresis: thermodynamics versus kinetics," Electrophoresis, 2017, 11 pages.

Marczak et al., "Simultaneous isolation and preconcentration of exosomes by icon concentration polarization," 2018, doi: 10.1002/elps.201700491.

Marczak, "Beyond Equilibrium—Using Ion Concentration Polarization to Enhance the Detection and Selectivity of Nucleic Acids and the Isolation of Exosomes," Department of Chemical and Biomolecular Engineering, University of Notre Dame, 2017.

Mathivanan et al., "Proteomics analysis of A33 immunoaffinity-purified exosomes released from the human colon tumor cell line LIM1215 reveals a tissue-specific protein signature," Mol. Cell. Proteomics, 2010, 9, 197-208.

Michael et al., "Exosomes from human saliva as a source of microRNA biomarkers," Oral Discovery, 2010, 16, 34-38.

Milane et al., "Exosome mediated communication within the tumor microenvironment," J. Control Release, 2015, 219, 278-294.

Minciacchi et al., "Extracellular vesicles in cancer: exosomes, microvesicles and the emerging role of large oncosomes," Semin. Cell Dev. Biol., 2015, 40, 41-51.

Minerick et al., "Electrokinetic transport of red blood cells in microcapillaries," Electrophoresis, 2002, 23, 2165-2173.

Moghadam et al., "Two orders of magnitude improvement in detection limit of lateral flow assays using isotachophoresis," Anal. Chem., 2015, 87, 1009-1017.

Momen-Heravi et al., "Current methods for the isolation of extracellular vesicles," Biol. Chem., 2013, 394, 1253-1262.

Pan et al., "Electrochemical DNA biosensor based on a glassy carbon electrode modified with gold nanoparticles and graphene for sensitive determination of Klebsiella pneumoniae carbapenemase," J. Biotechnol., 2015, 214, 133-138.

Parolo et al., "Enhanced lateral flow immunoassay using gold nanoparticles loaded with enzymes," Biosensors & Bioelectronics, 2013, 40, 412-416.

Patel et al., "High resolution of microRNA signatures in human whole saliva," Arch. Oral Biol., 2011, 56, 1506-1513.

Peinado et al., "Melanoma exosomes educate bone marrow progenitor cells toward a pro-metastatic phenotype through MET," Nat. Med., 2012, 18, 883-891.

Pernodet et al., "Pore size of agarose gels by atomic force microscopy," Electrophoresis, 1997, 18, 55-58.

Praus et al., "Capillary isotachophoresis for separation of silver nanoparticles according to size," RSC Adv., 2015, 5, 59131-59136.

(56) References Cited

OTHER PUBLICATIONS

Pyell et al., "Calibration-free concentration determination of charged colloidal nanoparticles and determination of effective charges by capillary isotachophoresis," Anal. Bioanal. Chem., 2009, 395, 1681-1691.
Quist et al., "Single-Electrolyte Isotachophoresis Using a Nanochannel-Induced Depletion Zone," Anal. Chem., 2011, 83, 7910-7915.
Quist et al., "Tunable Ionic Mobility Filter for Depletion Zone Isotachophoresis," Anal. Chem., 2012, 84, 9065-9071.
Rabinowits et al., "Exosomal microRNA: a diagnostic marker for lung cancer," Clin. Lung Cancer, 2009, 10, 42-46.
Ravan et al., "Strategies for optimizing DNA hybridization on surfaces," Anal. Biochem., 2014, 444, 41-46.
Ray, "Pancreatic cancer exosomes prime the liver for metastasis," Nat. Rev. Gastroenterol Hepatol., 2015, 12, 371.
Richards et al., "Cancer-associated fibroblast exosomes regulate survival and proliferation of pancreatic cancer cells," Oncogene, 2017, 36, 1770-1778.
Richards et al., "Integrated Microfluidics Device for Exosome Concentration, Lysis and RNA Quatification for Cancer Diagnosis," HCRI Science Day, 2017.
Righetti et al., "On the limiting pore size of hydrophilic gels for electrophoresis and isoelectric focusing," J. Biochem. Biophys. Methods, 1981, 4, 347-363.
Rohrman et al., "A Lateral Flow Assay for Quantitative Detection of Amplified HIV-1 RNA," PLoS One, 2012, 7(9), e45611, 8 pages.
Schneider et al., Advancements of Mass Spectrometry in Biomedical Research, 2014, 808, 399-408.
Schultz et al., "MicroRNA Biomarkers in Whole Blood for Detection of Pancreatic Cancer," J. Am. Med. Assoc., 2014, 311, 392-404.
Sedighi et al., "A Proposed Mechanism of the Influence of Gold Nanoparticles on DNA Hybridization," ACS Nano, 2014, 8 (7), 6765-6777.
Senapati et al., "An Ion-Exchange Nanomembrane Sensor for Detection of Nucleic Acids using a Surface Charge Inversion Phenomenon," Biosensors & Bioelectronics, 2014, 60, 92-100.
Skog et al., "Glioblastoma microvesicles transport RNA and proteins that promote tumour growth and provide diagnostic biomarkers," Nat. Cell Biol., 2008, 10, 1470-1476.
Slouka et al., "Charge inversion, water splitting, and vortex suppression due to DNA sorption on ion-selective membranes and their ion-current signatures," Langmuir, 2013, 29, 8275-8283.
Slouka et al., "Microfluidic Systems with Ion-Selective Membranes," Annual Review of Analytical Chemistry, 2014, 7, 317-335.
Soliman et al., "Monitoring potential prostate cancer biomarkers in urine by capillary electrophoresis-tandem mass spectrometry," J. Chromatogr. A., 2012, 1267, 162-169.
Sun et al., "Concentration-Gradient Stabilization with Segregated Counter- and Co-Ion Paths: A Quasistationary Depletion Front for Robust Molecular Isolation or Concentration," Physical Review Applied, 2017, 7: 064024.
Sun et al., "High-flux ionic diodes, ionic transistors and ionic amplifiers based on external ion concentration polarization by an ion exchange membrane: a new scalable ionic circuit plataform," Lab Chips, 2016, 16, 1171.
Swarup et al., "Circulating (cell-free) nucleic acids—a promising, non-invasive tool for early detection of several human diseases," FEBS Lett., 2007, 581, 795-799.
Taller et al., "On-chip surface acoustic wave lysis and ion-exchange nanomembrane detection of exosomal RNA for pancreatic cancer study and diagnosis," Lab. Chip, 2015, 1656-1666.
Tauro et al., "Comparison of ultracentrifugation, density gradient separation, and immunoaffinity capture methods for isolating human colon cancer cell line LIM1863-derived exosomes," Methods, 2012, 293-304.
Taylor et al., "MicroRNA signatures of tumor-derived exosomes as diagnostic biomarkers of ovarian cancer," Gynecol Oncol., 2008, 110, 13-21.
Tickner et al., "Functions and Therapeutic Roles of Exosomes in Cancer," Front Onco., 2014, 4, 127, 8 pages.
Torphy et al., "Circulating tumor cells as a biomarker of response to treatment in patient-derived xenograft mouse models of pancreatic adenocarcinoma," PLos One, 2014, 9, 89474, 7 pages.
Traver et al., "Cell-free nucleic acids as non-invasive biomarkers of gynecological cancers, ovarian, endometrial and obstetric disorders and fetal aneuploidy," Hum. Reprod. Update, 2014, 20 (6), 905-923.
Vaidyanathan et al., "Detecting exosomes specifically: a multiplexed device based on alternating current electrohydrodynamic induced nanoshearing," Anal. Chem., 2014, 86, 11125-11132.
Van Deun et al., "The impact of disparate isolation methods for extracellular vesicles on downstream RNA profiling," J. Extracell. Vesicles, 2014, 3, 24858, 14 pages.
Vogelstein et al., "Cancer genome landscapes," Science, 2013, 339, 1546-1558.
Wang et al., "Ciliated micropillars for the microfluidic-based isolation of nanoscale lipid vesicles," Lab Chip, 2013, 13, 2879-2882.
Wang et al., "Dynamic superconcentration at critical-point double-layer gates of conducting nanoporous granules due to asymmetric tangential fluxes," Biomicrofluidics, 2008, 2: 014102.
Webber et al., "Differentiation of tumour-promoting stromal myofibroblasts by cancer exosomes," Oncogene, 2015, 34, 319-331.
Weiner, Microvesicles and Liposomes, Application Note, Brookhaven Instruments, A Nova Instruments Company. 2013.
Whiteside, "Tumor-Derived Exosomes and Their Role in Cancer Progression," Adv. Clin. Chem., 2016, 74, 103-141.
Wijenayaka et al., "Improved Parametrization for Extended Derjaguin, Landau, Verwey, and Overbeek Predictions of Functionalized Gold Nanosphere Stability," J. Phys. Chem. C, 2015, 119, 10064-10075.
Willms et al., "Cells release subpopulations of exosomes with distinct molecular and biological properties," Sci. Rep., 2016, 6, 22519, 12 pages.
Wu et al., "Two-step size- and shape-separation of biosynthesized gold nanoparticles." Separation and Purification Technology, 2013, 106, pp. 117-122.
Xu et al., "Size and shape separation of gold nanoparticles with preparative gel electrophoresis." Journal of Chromatography A, 2007, 1167, pp. 35-41.
Yamada et al., "Comparison of Methods for Isolating Exosomes from Bovine Milk," Clin. Pathol., 2012, 74, 1523-1525.
Yang et al., "Exosome separation using microfluidic systems: size-based, immunoaffinity-based and dynamic methodologies," Biotechnol. J., 2017, 12, 1600699, 8 pages.
Yu et al., "Tumor-derived exosomes in cancer progression and treatment failure," Oncotarget, 2015, 6 , 37151-37168.
Zanchet et al., "Electrophoretic Isolation of Discrete Au Nanocrystal/DNA Conjugates." Nano Letters, 2001, 1 (1), pp. 32-35.
Zhang et al., "Microenvironment-induced PTEN loss by exosomal microRNA primes brain metastasis outgrowth," Nature, 2015, 527, 100-104.
Zhao et al., "A microfluidic ExoSearch chip for multiplexed exosome detection towards blood-based ovarian cancer diagnosis," Lab Chip, 2016, 16, 489-496.
Zhou et al., "Immune-related microRNAs are abundant in breast milk exosomes," Int. J. Biol. Sci., 2012, 8, 118-123.
Zimmermann et al., "Salivary mRNA targets for cancer diagnostics," Oral Oncol., 2008, 44, 425-429.

* cited by examiner

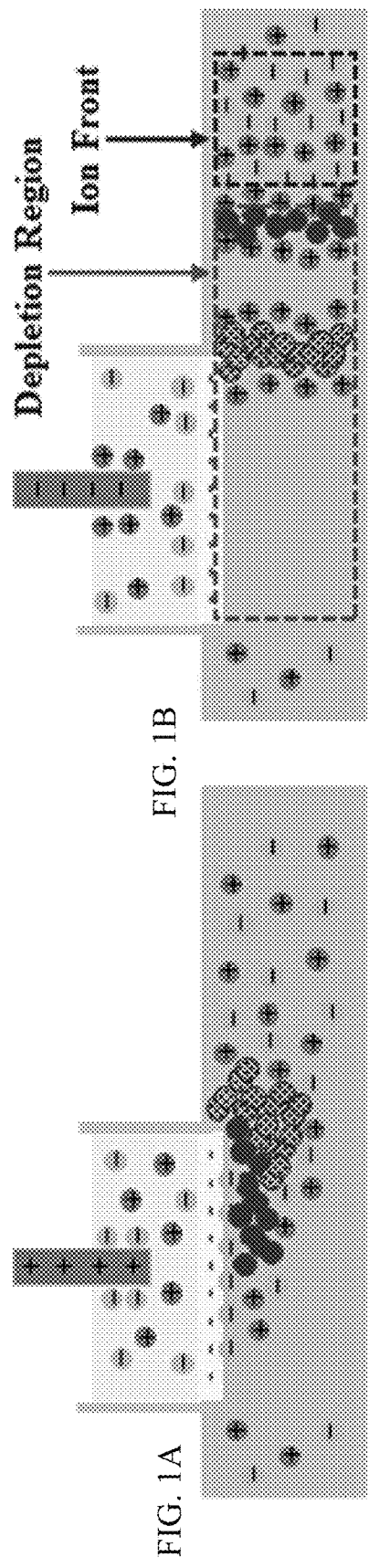
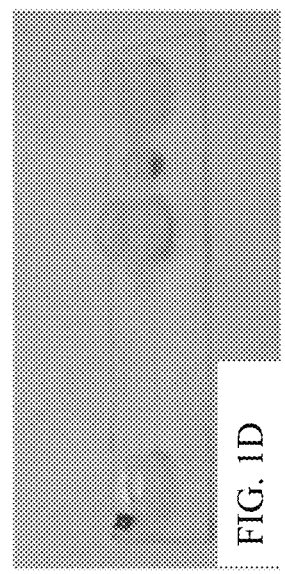
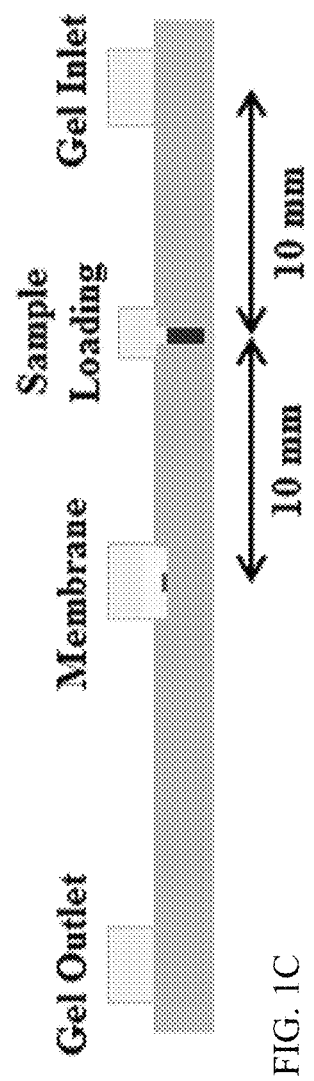
FIGS. 1A-1D

```
                            SEQUENCE LISTING

<160> NUMBER OF SEQ ID NOS: 9

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
tggttctctc cgaaatagct ttagggta                                      28

<210> SEQ ID NO 2
<211> LENGTH: 35
<212> TYPE: DNA
<213> ORGANISM: Artificial Sequence
<220> FEATURE:
<223> OTHER INFORMATION: Synthetic

<400> SEQUENCE: 2
gaagggaaga ggaagaggca ggtgtcctgt ggtag                              35

<210> SEQ ID NO 3
<211> LENGTH: 69
<212> TYPE: DNA
<213> ORGANISM: Artificial Sequence
<220> FEATURE:
<223> OTHER INFORMATION: Synthetic

<400> SEQUENCE: 3
ctaccacagg acacctgcct cttcctcttc ccttcaaaaa tagccctaaa gctatttcgg   60
agagaacca                                                           69

<210> SEQ ID NO 4
<211> LENGTH: 69
<212> TYPE: DNA
<213> ORGANISM: Artificial Sequence
<220> FEATURE:
<223> OTHER INFORMATION: Synthetic

<400> SEQUENCE: 4
gctggcactc tacactagaa gggatagata tgccaaaaaa accaaatttc aggcccggaa   60
ctttcttgc                                                           69

<210> SEQ ID NO 5
<211> LENGTH: 29
<212> TYPE: DNA
<213> ORGANISM: Artificial Sequence
<220> FEATURE:
<223> OTHER INFORMATION: Synthetic

<400> SEQUENCE: 5
tggttctctc cgaaatagct ttagggcta                                     29

<210> SEQ ID NO 6
<211> LENGTH: 69
<212> TYPE: DNA
<213> ORGANISM: Artificial Sequence
<220> FEATURE:
<223> OTHER INFORMATION: Synthetic

<400> SEQUENCE: 6
```

```
ctaccgtagg acacctgcct cttcctcttc ccttcaaaaa tagccctaaa gctatttcgg    60
aggcaacca                                                             69

<210> SEQ ID NO 7
<211> LENGTH: 69
<212> TYPE: DNA
<213> ORGANISM: Artificial Sequence
<220> FEATURE:
<223> OTHER INFORMATION: Synthetic

<400> SEQUENCE: 7
ctaccacagg acacctgcct cttcctcttc cctataaaaa aggccctaaa gctatttcgg    60
agagaacca                                                             69

<210> SEQ ID NO 8
<211> LENGTH: 69
<212> TYPE: DNA
<213> ORGANISM: Artificial Sequence
<220> FEATURE:
<223> OTHER INFORMATION: Synthetic

<400> SEQUENCE: 8
ctattgtagg acacctgcct cttcctcttc ccttcaaaaa tagccctaaa gctatttcgg    60
aggcggcca                                                             69

<210> SEQ ID NO 9
<211> LENGTH: 69
<212> TYPE: DNA
<213> ORGANISM: Artificial Sequence
<220> FEATURE:
<223> OTHER INFORMATION: Synthetic

<400> SEQUENCE: 9
ctaccacagg acacctgcct cttcctcttc ctaataaaaa agttcctaaa gctatttcgg    60
agagaacca                                                             69
```

ULTRA-SENSITIVE MULTI-TARGET LATERAL FLOW MOLECULAR ASSAY WITH FIELD-INDUCED PRECIPITATION

CROSS-REFERENCE TO RELATED APPLICATIONS

This claims priority to U.S. Provisional Patent Application No. 62/513,142, filed on May 31, 2017, the entire contents of which are fully incorporated herein by reference.

TECHNICAL FIELD

The present disclosure relates to a method for concentrating, separating, and quantifying biomolecules such as polynucleotides or polypeptides using ion concentration polarization and nanoparticle aggregation.

BACKGROUND OF THE INVENTION

The ability to detect and quantify low-abundance biomolecules, including antigens, antibodies, receptors, ligands and nucleic acids, in ultra-small volumes of complex biological matrices, including samples from single cells, is critical to many disciplines, such as medical diagnostics, environmental monitoring and chemical analysis. To address this challenge, efficient concentration and separation techniques are critically needed.

Typical methods for detecting biomolecules utilize specific binding between a target biomolecule and a corresponding binding partner to form a readily detectable complex. Many electrochemical and colorimetric approaches rely on equilibrium-based assays. However, these assays can take hours or more often days of waiting to reach equilibrium which significantly slows down throughput. The detection and capture moieties, such as ssDNA probes or antibodies, may have relatively high dissociation constants restricting the limit of detection to concentrations above the desired range, and resulting in poor sensitivity. Dissociation constants between intended and non-intended binding partners are usually very similar and thus lead to poor selectivity and false positive signals in many of the current assays.

Accordingly, there is a need in the art for methods that improve the sensitivity, speed and simplicity of biomolecule detection, and especially for those that are readily adaptable for detecting a wide variety of biomolecules.

BRIEF SUMMARY OF THE INVENTION

Disclosed herein are methods for separating biomolecules. The methods comprise (a) providing a microfluidic device comprising a microchannel having a first end and a second end and containing an electrophoresis matrix, an ion permselective membrane in direct contact with the electrophoresis matrix, and first and second electrodes configured to apply an electric field across the ion permselective membrane, (b) loading a sample containing a plurality of biomolecules, a plurality of first probes and a plurality of second probes into the electrophoresis matrix, wherein each of the first probes comprises a first nanoparticle coupled to a plurality of first binding moieties, and each of the second probes comprises a second nanoparticle coupled to a plurality of second binding moieties, and wherein the first binding moieties and second binding moieties are configured to bind target biomolecules within the plurality of biomolecules, (c) applying a first electric field that causes the plurality of biomolecules, the plurality of first probes and the plurality of second probes to move through the electrophoresis matrix towards the ion permselective membrane whereupon the plurality of biomolecules, the plurality of first probes and the plurality of second probes become concentrated in the electrophoresis matrix adjacent to the ion permselective membrane, wherein at least some of the target biomolecules bind to one of the plurality of first probes and one of the plurality of second probes to form a plurality of linked nanoparticle multimers comprising at least one first nanoparticle and at least one second nanoparticle, and (d) applying a second electric field to form an ion depletion front as a result of ion concentration polarization, whereupon the ion depletion front moves away from the ion permselective membrane and whereupon linked nanoparticle multimers at the ion depletion front aggregate and precipitate and whereupon biomolecules, first probes and second probes not contained within a linked nanoparticle multimer move through the electrophoresis matrix away from the ion permselective membrane behind the ion depletion front.

BRIEF DESCRIPTIONS OF THE DRAWINGS

FIGS. 1A-1D are schematics of the mechanism of nanoparticle separation. Enrichment (FIG. 1A): An electric field drives the particles towards the membrane and packs them at its surface. Depletion (FIG. 1B): The field is reversed, a depletion region forms, and the multimer particles aggregate while the monomer particles are driven away. Side view schematic of entire microfluidic chip (FIG. 1C). Chip filled with fluorescein-doped agarose gel and nanoparticles in the sample reservoir (FIG. 1D).

Figure 2B:
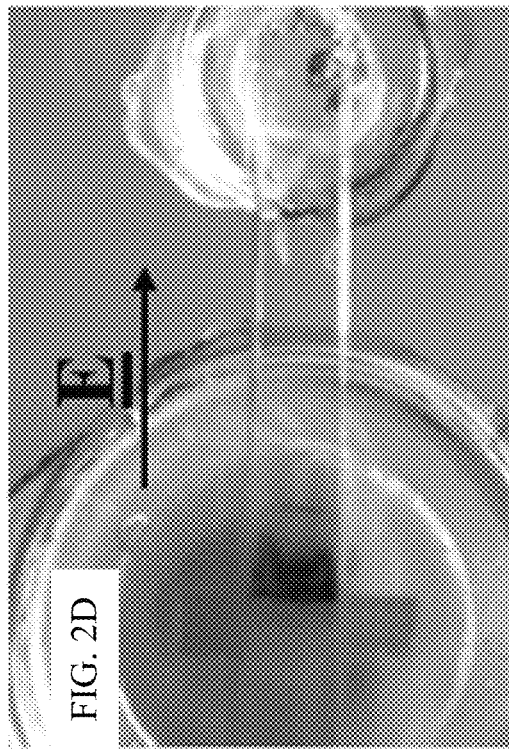
Figure 2C:
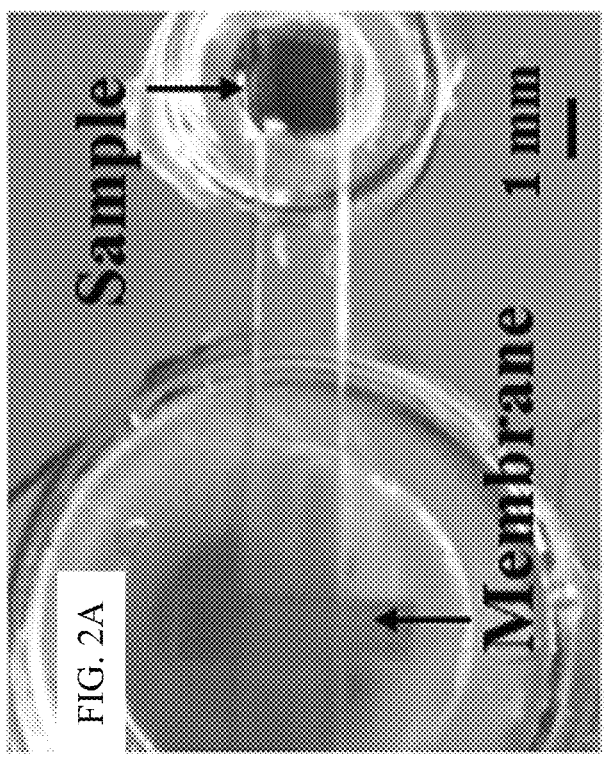
Figure 2D:
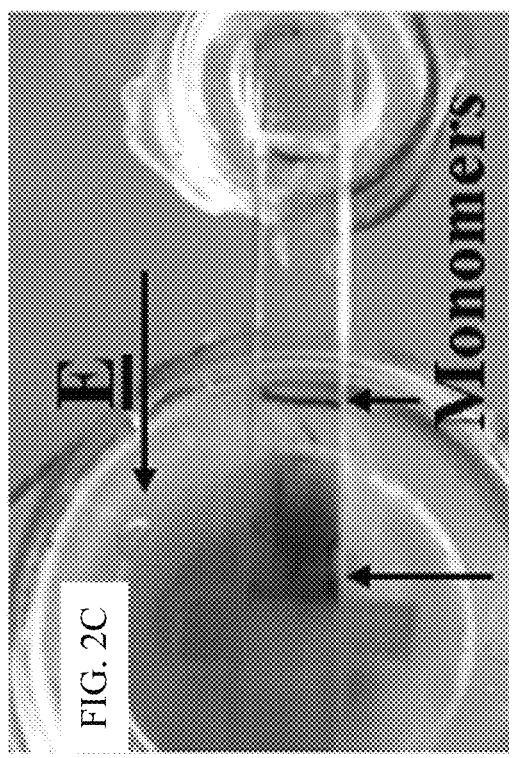

FIGS. 2A-2D are images showing an example separation of a sample with 10 nM target. Nanoparticle/DNA mixture is inserted into sample inlet (FIG. 2A). Sample packs tightly against the membrane during the enrichment step (FIG. 2B). Five minutes into the depletion step, the uncaptured monomer particles separate from the now aggregated multimer particles linked by target molecules. The monomer particles continue to migrate up the channel as a thin line at the front of the depletion region (FIG. 2C). The aggregated particles are repacked against the membrane for detection (FIG. 2D).

Figure 3:
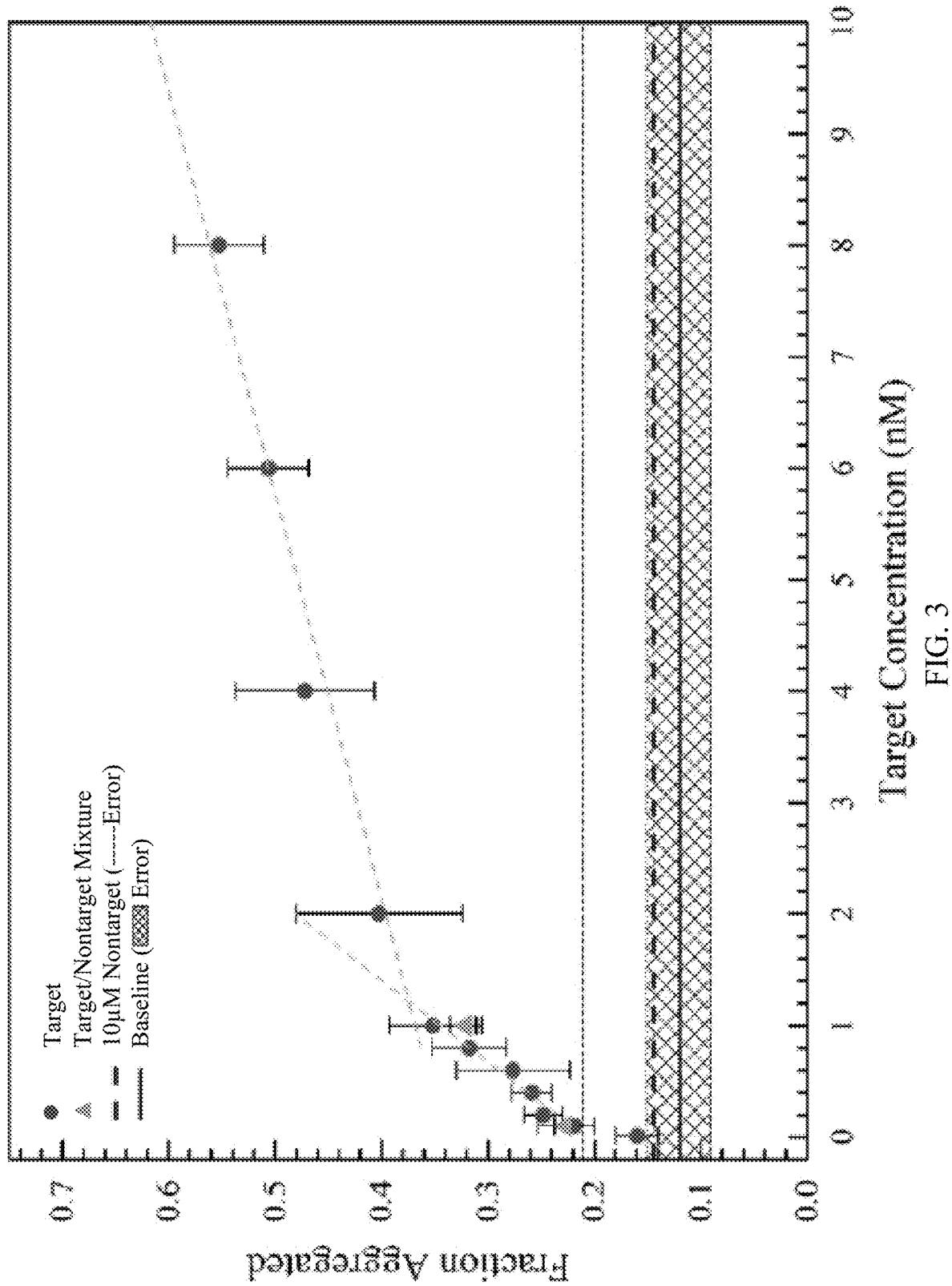

FIG. 3 is a calibration curve showing the fraction of aggregation as a function of DNA concentration. The target/nontarget mixture points possess a nontarget-to-target ratio of 10,000:1. The baseline signal corresponds to the nanoparticle mixture without either target or nontarget. Linear fits are shown from 100 pM to 1 nM and 1 nM to 8 nM with correlation coefficients of 0.96 and 0.98, respectively. Error bars represent uncertainties within a 95% confidence interval and n=4.

Figure 4:
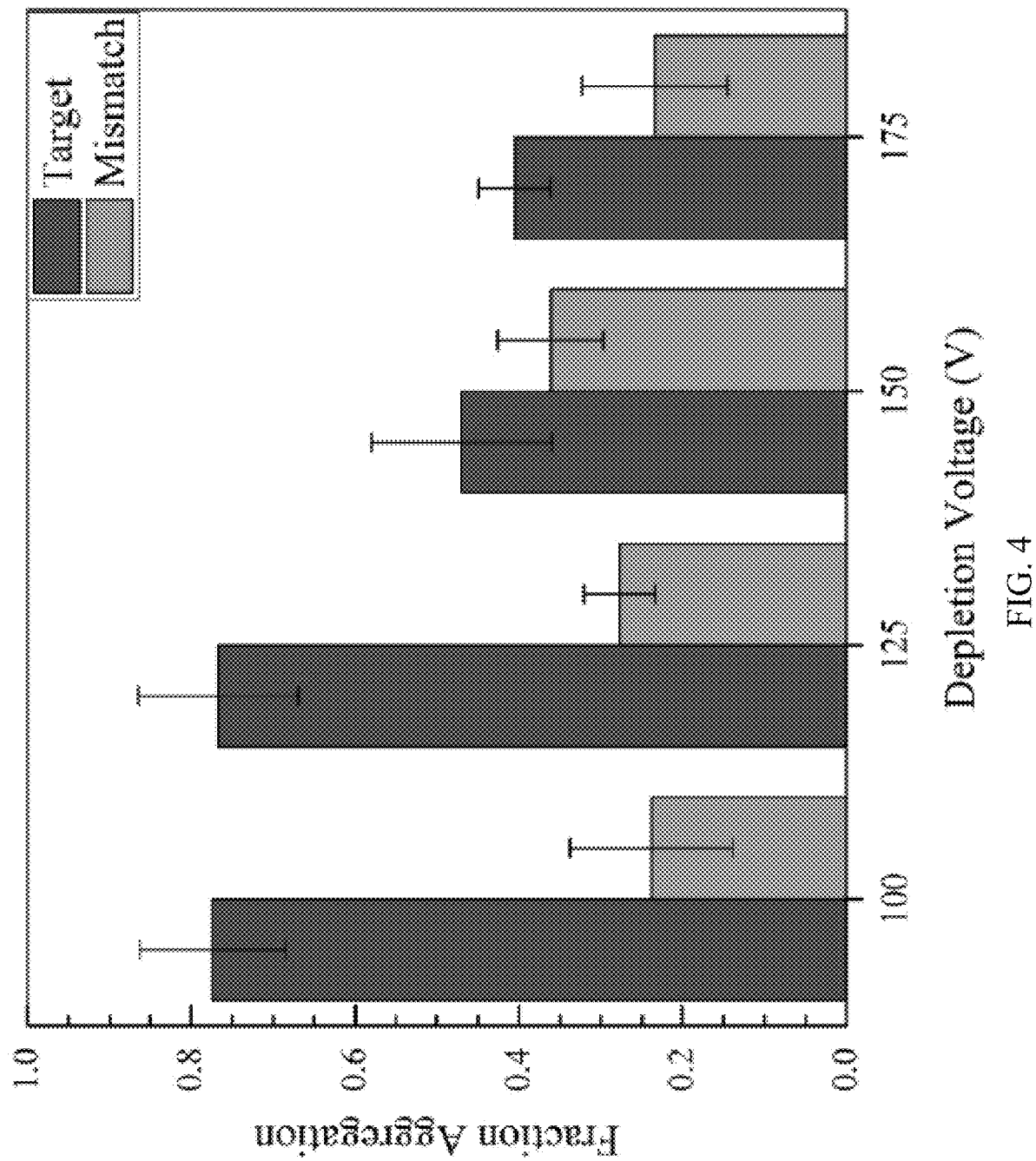

FIG. 4 is a bar graph showing the selectivity of the sensor for fully complementary target versus two-base pair mismatch target. The depletion voltage was initially applied at −200V potential for one minute followed by a step to change to different lower voltages. Error bars represent uncertainties within a 95% confidence interval and n=4.

Figure 5A:
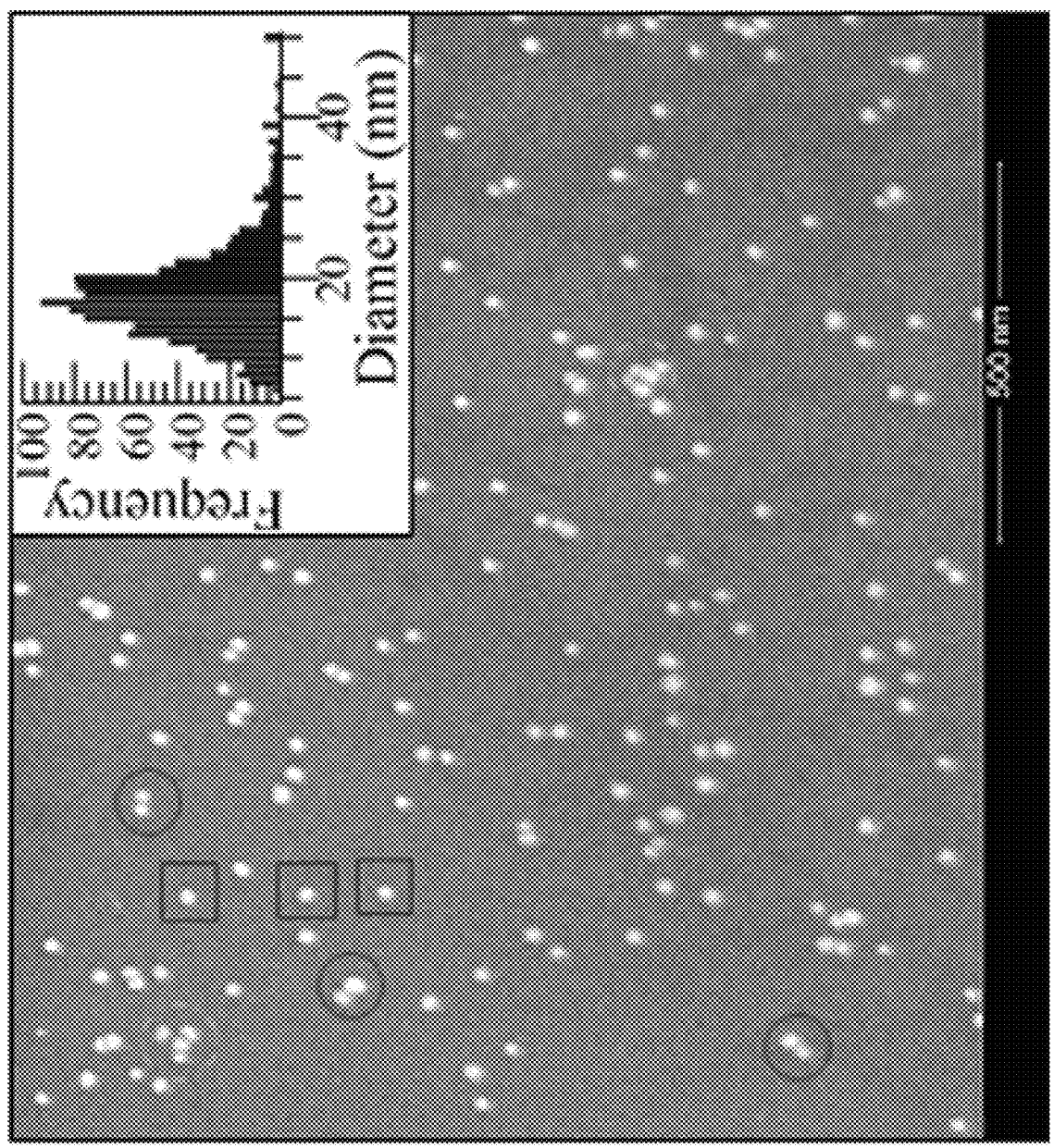
Figure 5B:
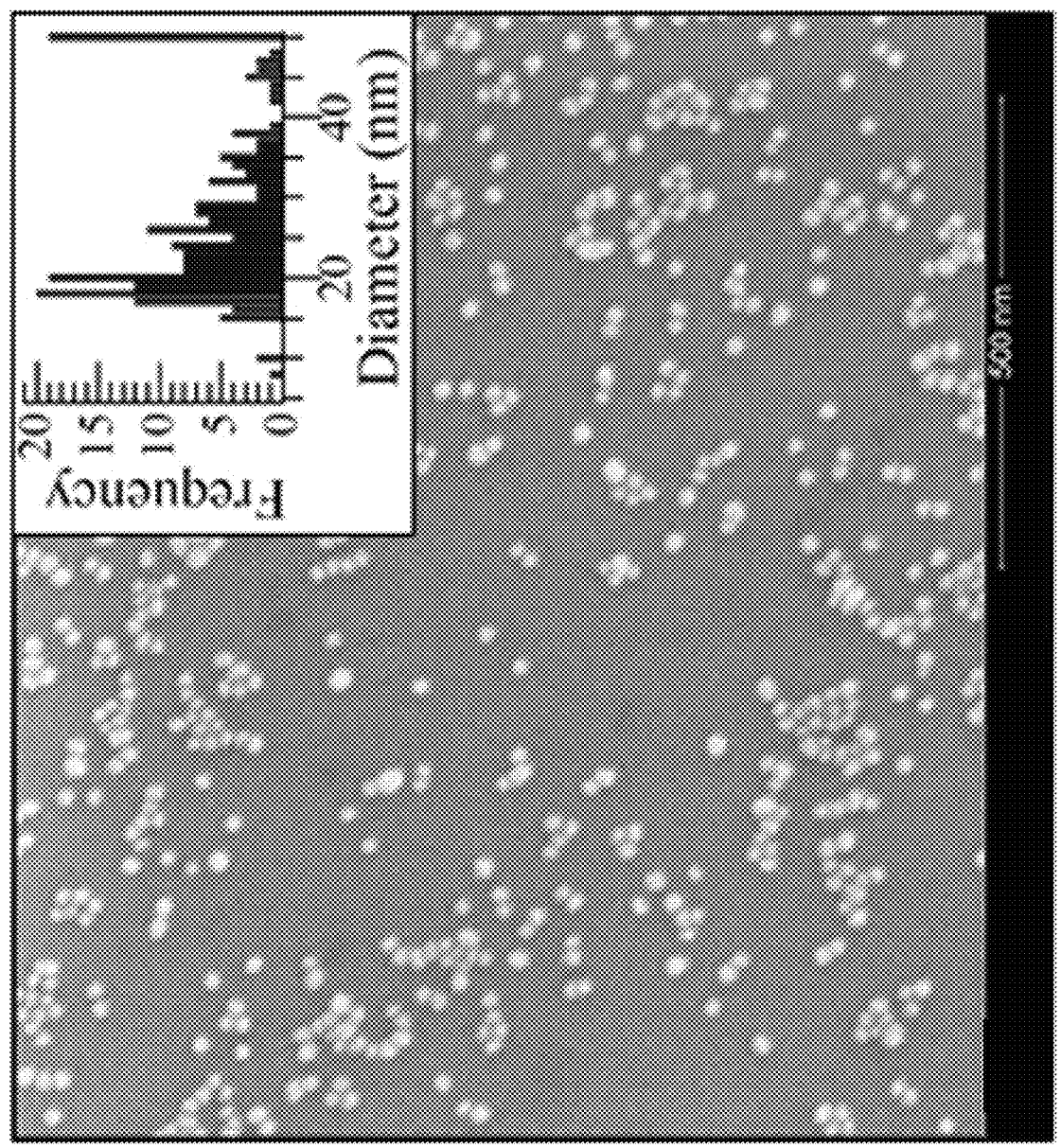

FIG. 5A and FIG. 5B are scanning electron microscopy (SEM) images showing nanoparticles from the monomer band (FIG. 5A) and aggregated band (FIG. 5B). Examples of different types of particles in the monomer band (FIG. 5A) are monomers shown by blue squares, dimers by red circles, and larger aggregates by broken green circles. The insets are representative histograms of particle diameters from each respective band.

Figure 6A:
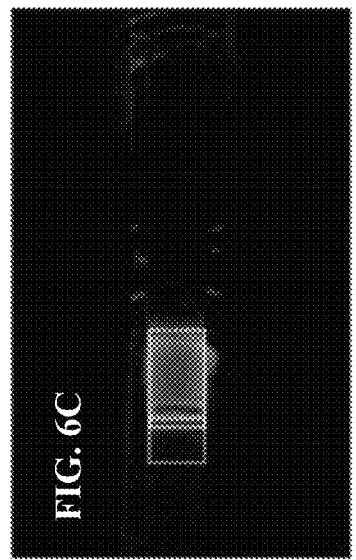
Figure 6B:
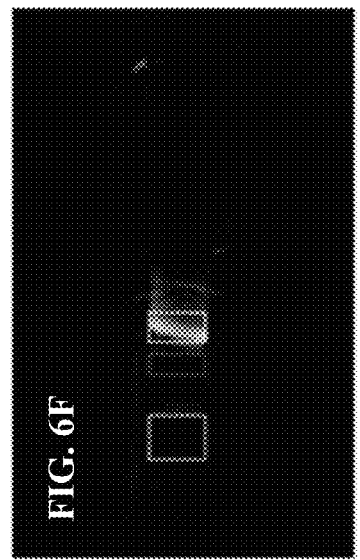
Figure 6C:
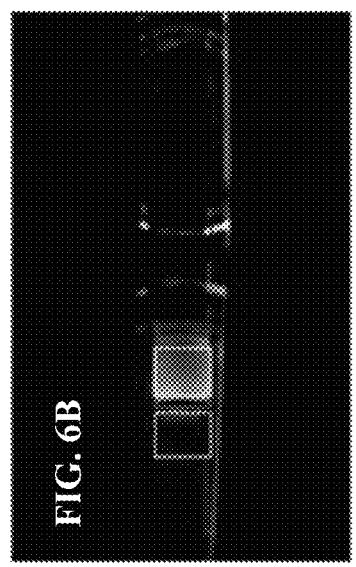
Figure 6D:
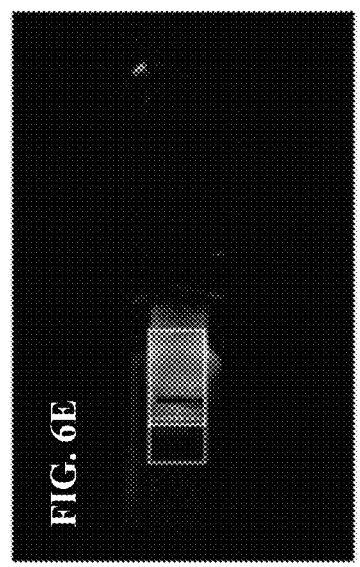
Figure 6E:
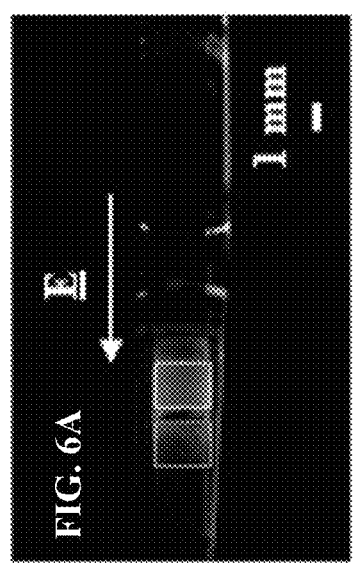
Figure 6F:
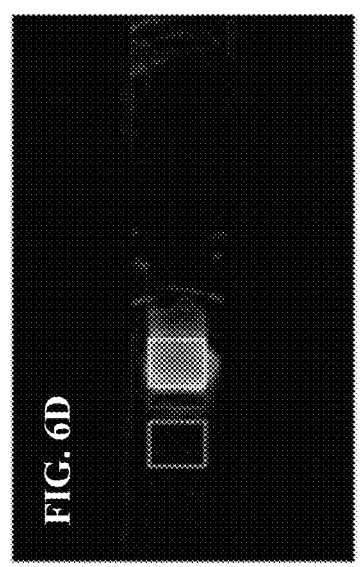

FIGS. 6A-6F are images showing the depletion step in fluorescein doped gel. Positions of the membrane, nanoparticles, and ion front are indicated by the yellow, red, and white boxes, respectively. The depletion front, indicated by the concentrated fluorescein band, was isolated by image subtraction. Images were taken after 0 min (FIG. 6A), 3 min applied voltage (FIG. 6B), 15 min no voltage (FIG. 6C), 1 min applied voltage (FIG. 6D), 15 min no voltage (FIG. 6E), and 1 min applied voltage (FIG. 6F).

Figure 7B:
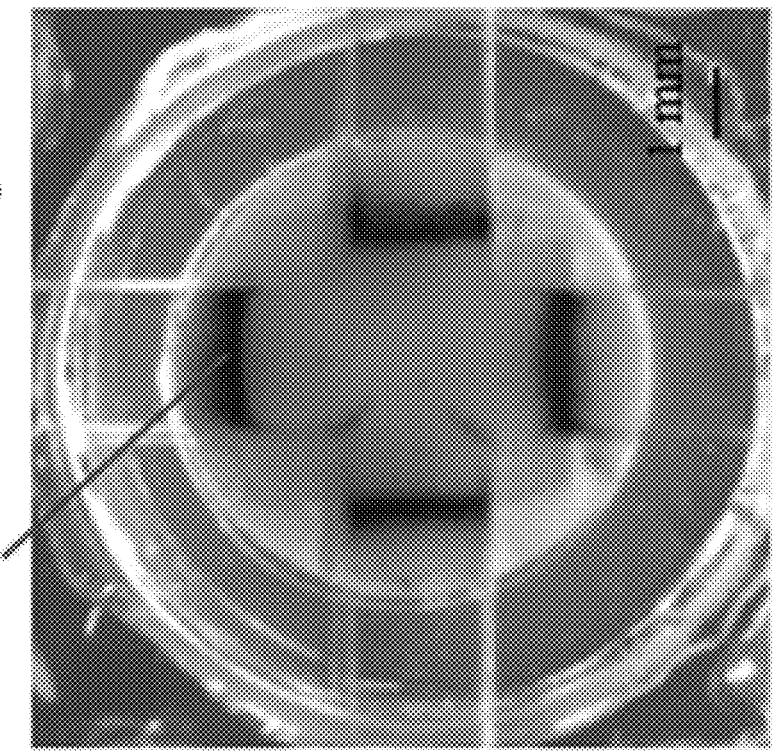
Figure 7A:
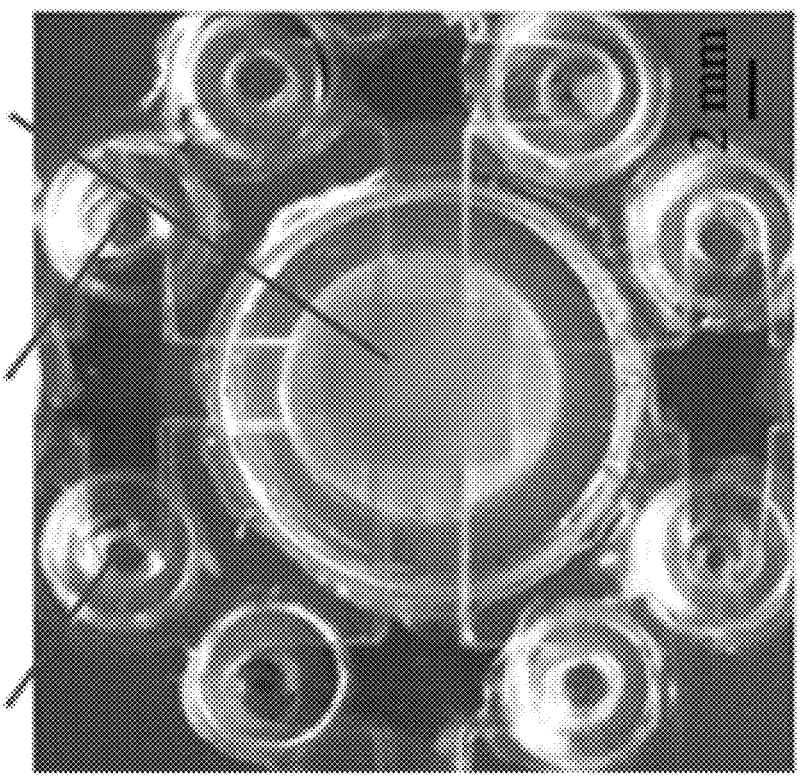
Figure 7D:
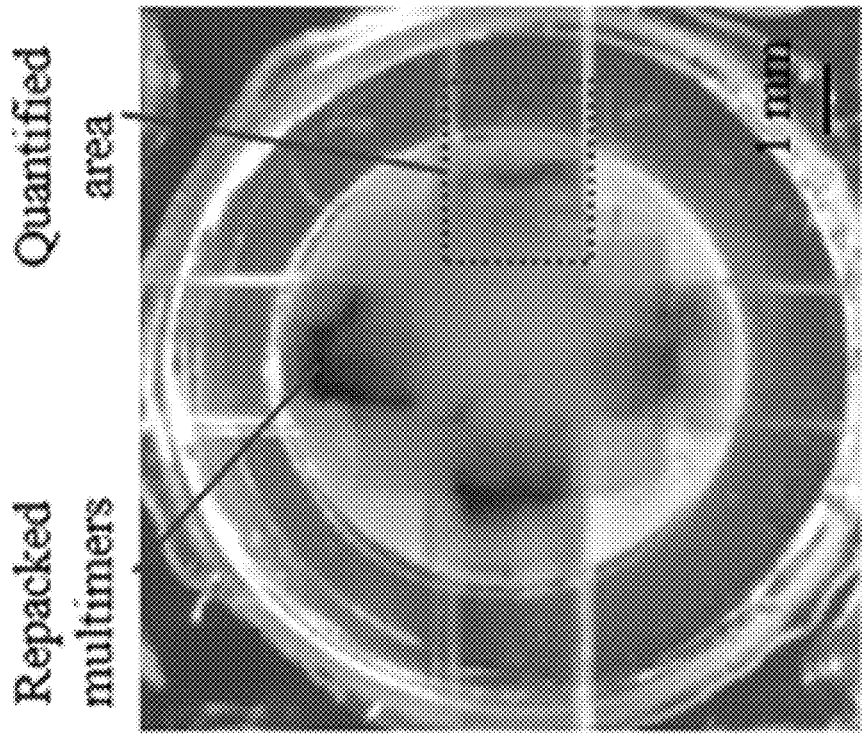
Figure 7C:
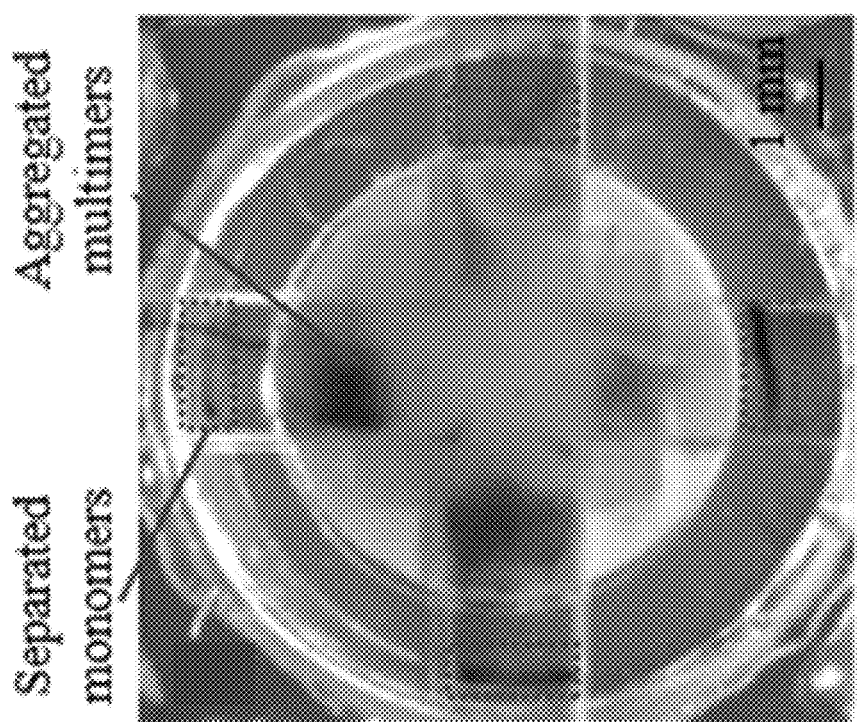
Figure 7E:
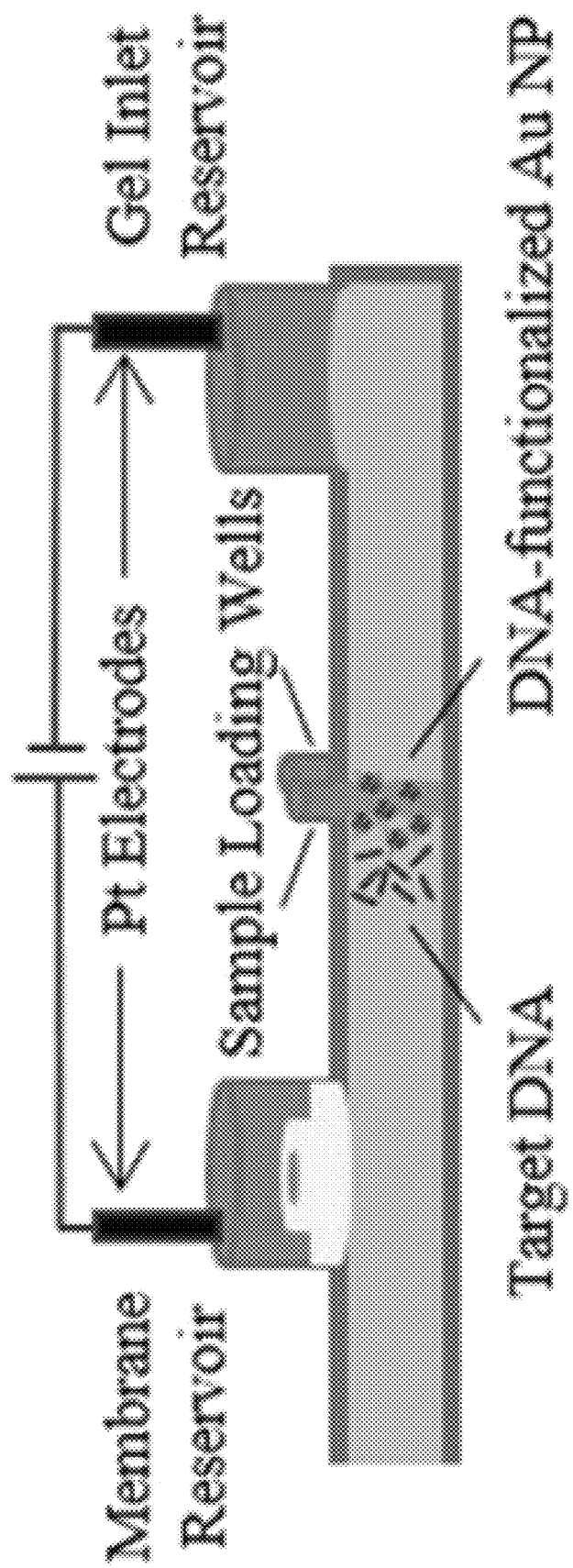

FIG. 7A, FIG. 7B, FIG. 7C, FIG. 7D and FIG. 7E are all images taken from below the chip. All images are taken with the same sample. Sample is loaded into cross-channel (FIG. 7A). Enrichment drives particles towards membrane (FIG. 7B). Depletion separates monomers from aggregate possessing target (FIG. 7C). Particles are repacked at membrane for quantification (FIG. 7D). Profile view of one channel (FIG. 7E). The three remaining channels intersect at the membrane and have identical electrode placement. CEM stands for cation-exchange membrane.

Figure 8B:
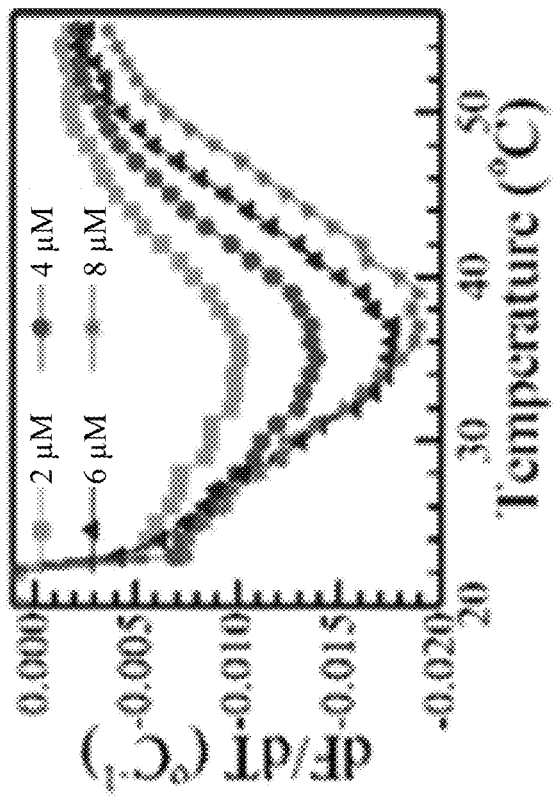
Figure 8A:
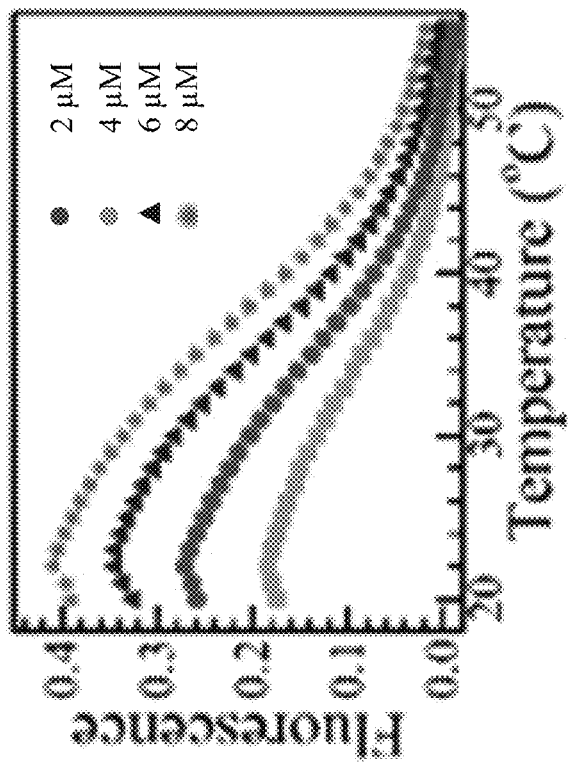
Figure 8C:
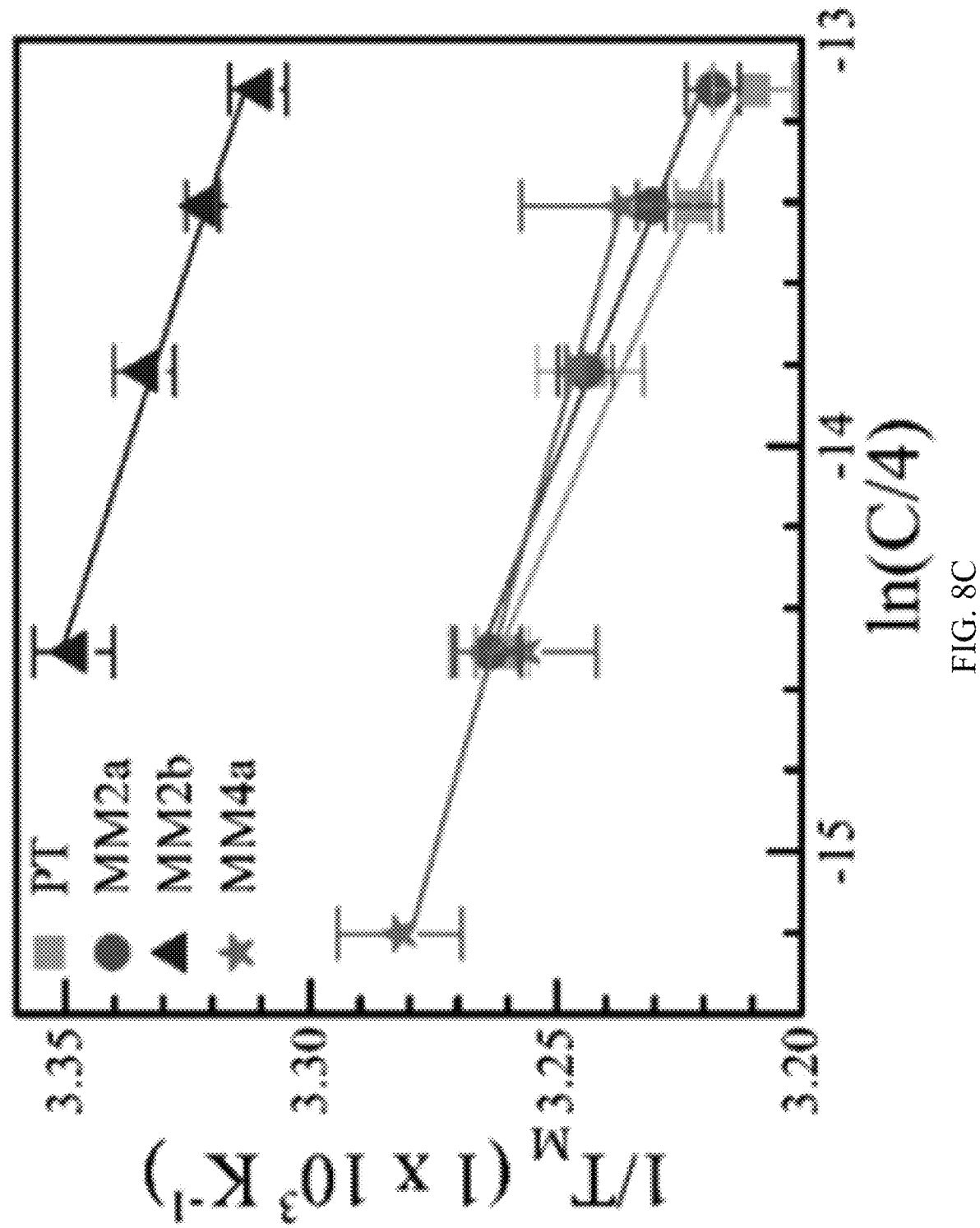

FIG. 8A, FIG. 8B and FIG. 8C are all graphs showing the analysis of the melting temperature of different DNA sequences functionalized to gold nanoparticles. FIG. 8A shows representative melting curves for the various concentrations of target, PT. Fluorescence intensity is in arbitrary units. FIG. 8B shows the corresponding first derivatives of the melting curves for the various concentrations of target, PT, where F is fluorescence intensity and T is temperature. Enthalpies and entropies of hybridization were derived from melting temperatures at different concentrations according to equation 1 (FIG. 8C). Coefficients of determination for linear fits are 0.97, 0.99, 0.98, and 0.96 for target, mismatch2a (MM2a), mismatch2b (MM2b), and mismatch4a (MM4a), respectively. Error bars are uncertainties within 95% confidence intervals and sample size n=5.

Figure 9:
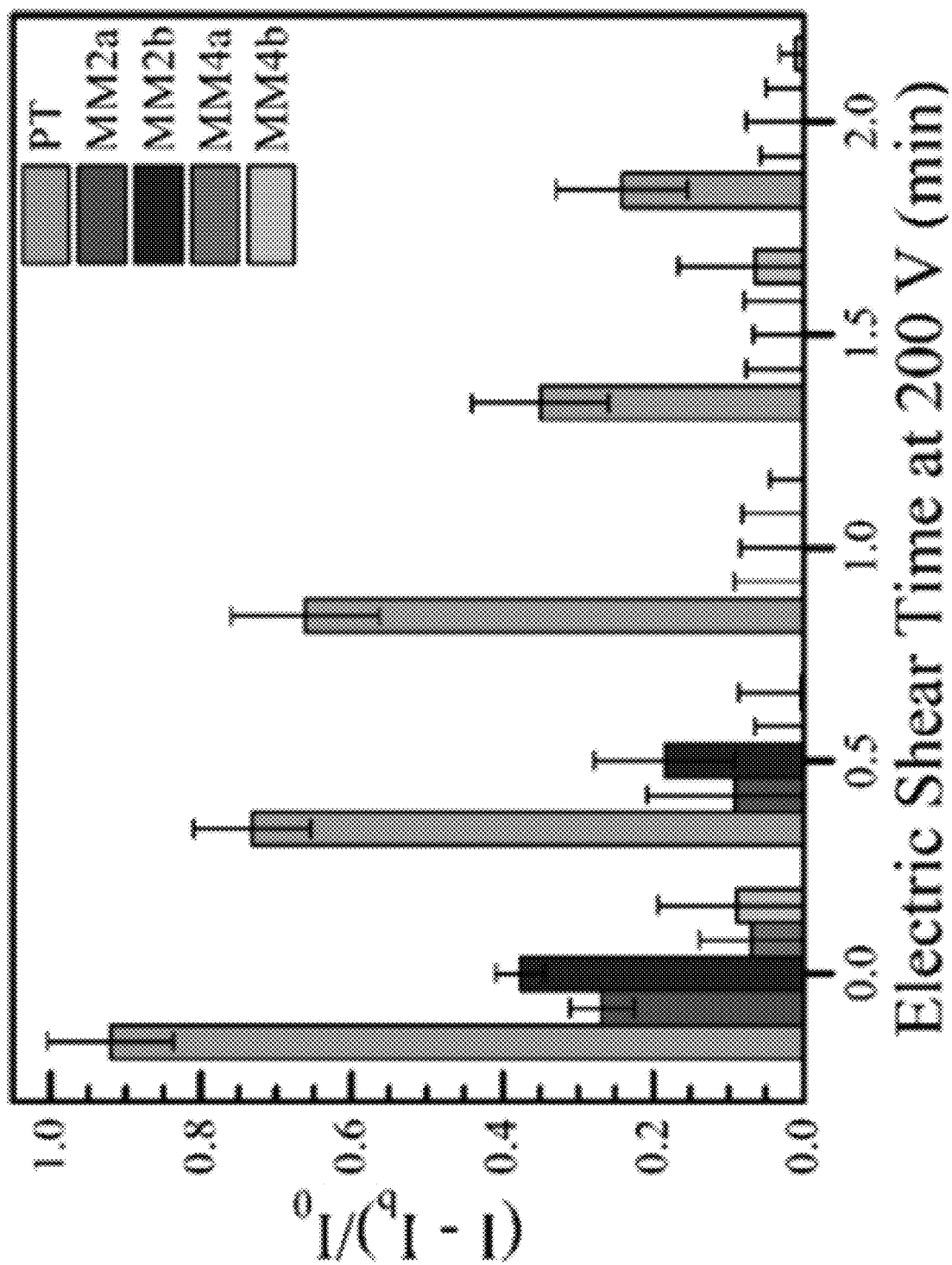

FIG. 9 is a bar graph showing selectivity improvements obtained by voltage ramping during depletion isotachophoresis. During depletion, the potential was applied at 200 V for various times (electric shear time) before ramping down to 125 V. $I_0$ is the initial particle intensity after enrichment, $I_b$ is the baseline aggregation (when no DNA is present), and I is the signal intensity for 10 nM DNA. Error bars represent uncertainties within 95% confidence intervals and sample size n=4.

Figure 10A:
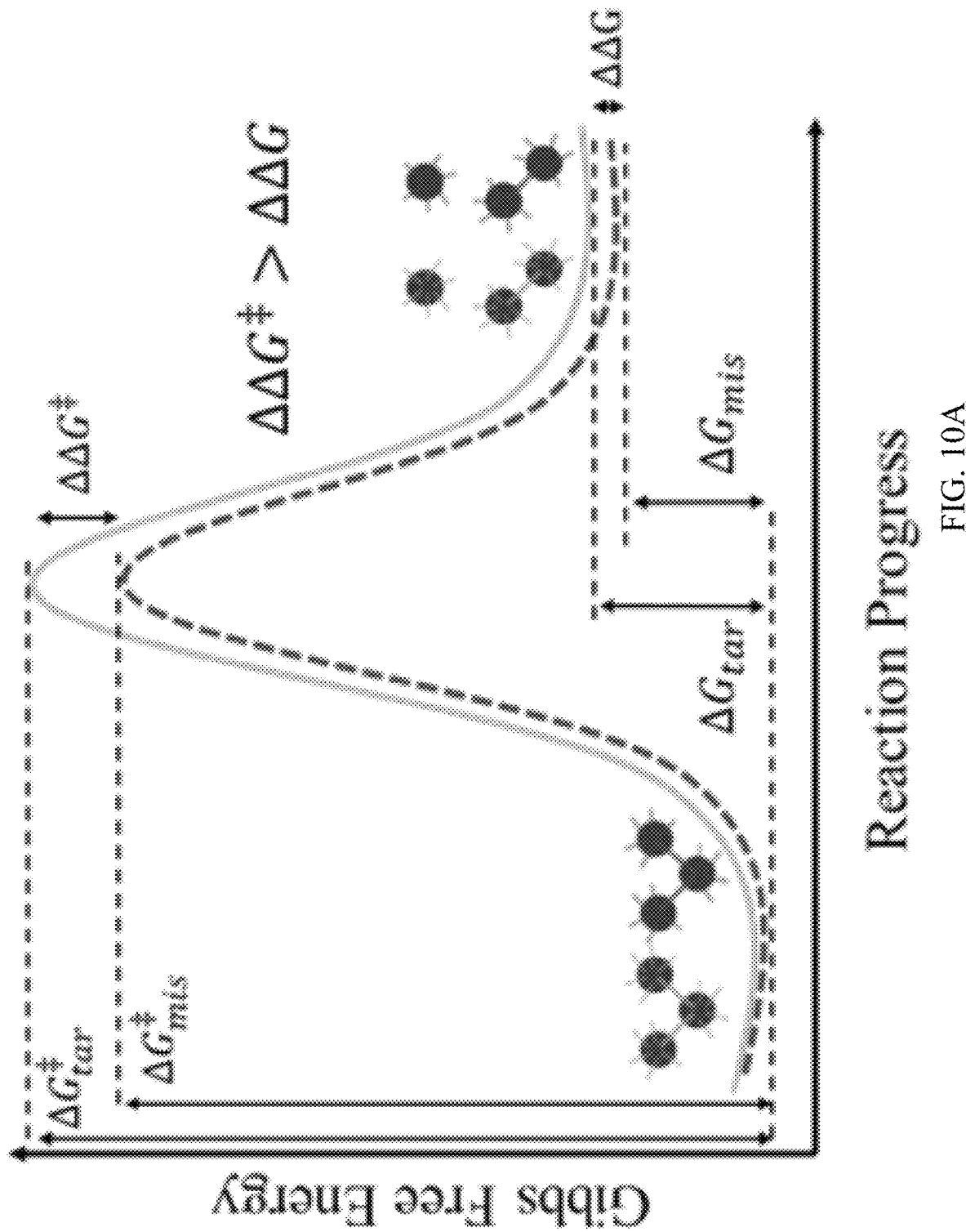
Figure 10B:
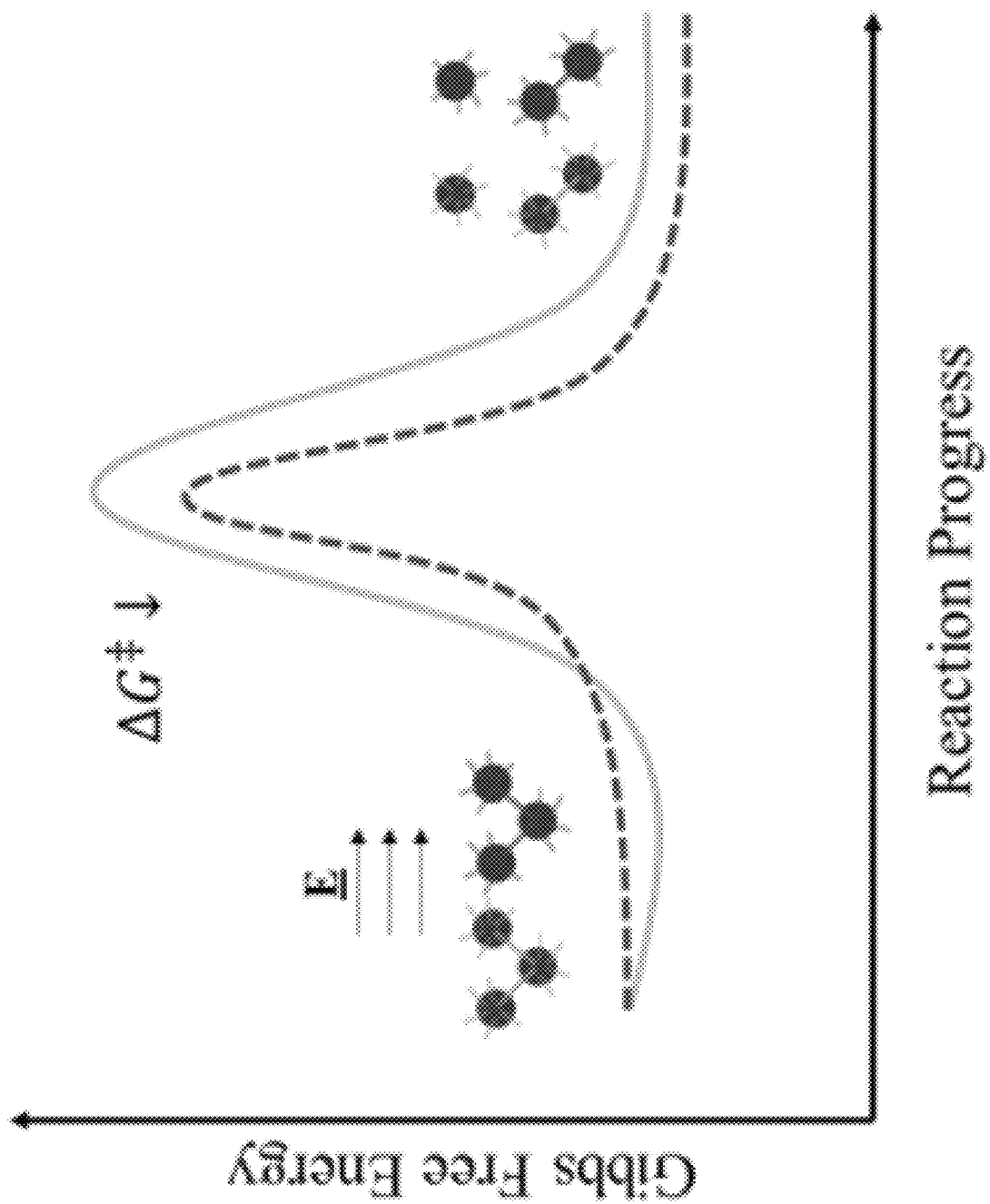
Figure 10C:
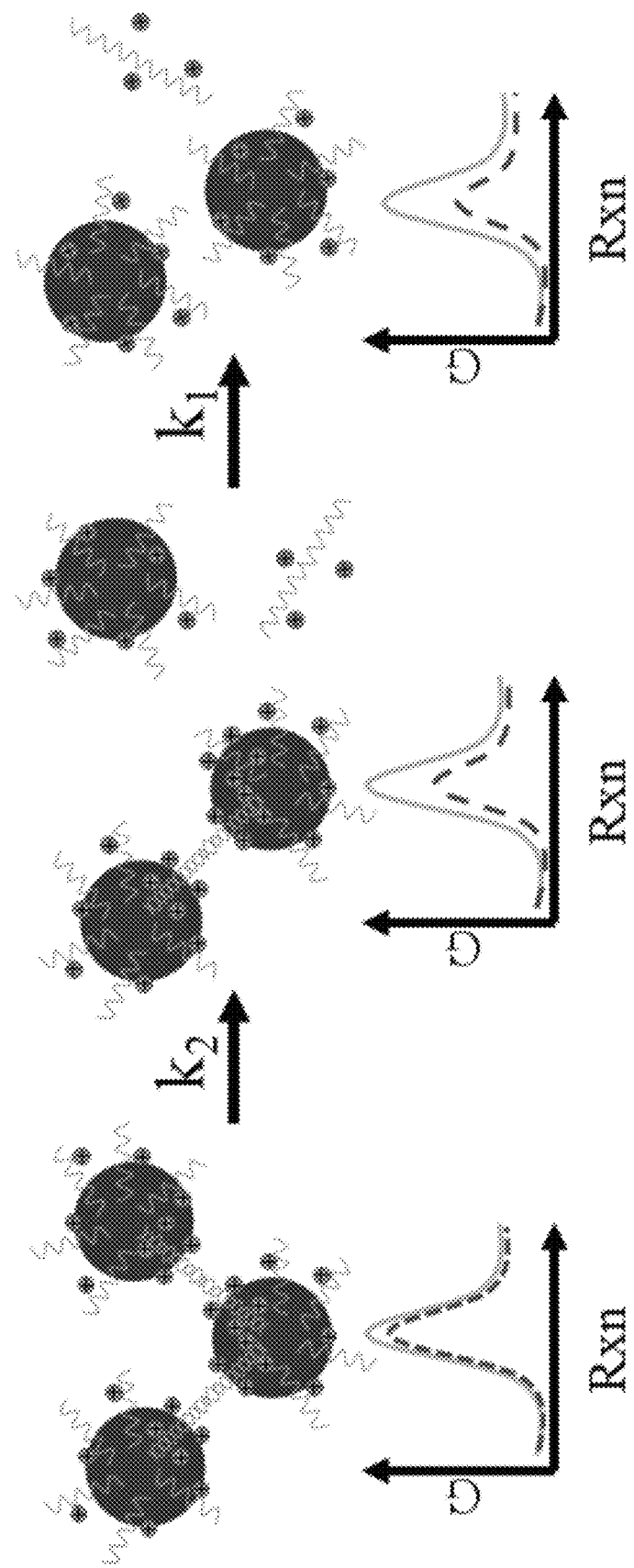

FIG. 10A, FIG. 10B and FIG. 10C are reaction coordinate diagrams for dehybridization for targets (green solid line) and mismatches (red dashed line). Duplexes face a significant energy barrier to dehybridization (FIG. 10A). Force from applied electric field destabilizes duplexes thereby raising initial energy and lowering $\Delta G^\ddagger$ (FIG. 10B). In the gel medium, electrical force on each nanoparticle of the duplex is often unequal due to field shielding and physical immobilization of one particle. Hence, the stretching force on the duplex should increase with electric field to destabilize it. Cooperative melting lowers energy barrier with each successive dehybridization such that $k_1 > k_2$ (FIG. 10C).

DETAILED DESCRIPTION OF THE INVENTION

The microfluidic-based assay described herein uses depletion isotachophoresis and nanoparticle aggregation to improve the limit of detection and sensitivity, decrease the time required for detection, and increase the selectivity compared to conventional equilibrium assays. Conventional equilibrium assays such as microarrays or lateral flow, which rely on diffusion to surface-based probes, possess poor sensitivity and little selectivity in comparison.

Preconcentrating the biomolecules and probes through ion concentration polarization favorably affects the binding of the biomolecules and binding moieties by driving the binding reaction in the forward direction while dramatically decreasing the effective dissociation constants. Using the aggregation of the nanoparticles prevents dissociation since the bound biomolecules are trapped within the aggregate. Concurrently, the electric field is able to dissociate any nonspecifically bound biomolecules and prevent their reassociation. Most importantly, since the preconcentration is driven by electrokinetics, using the disclosed method allows detection and quantification of biomolecules while reducing assay times from days to minutes.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Binding moiety" as used herein refers to a molecule that binds specifically or selectively to a target biomolecule. The binding moiety may be a nucleic acid, an aptamer, an avimer, receptor-binding ligands, binding peptides, protein, or small organic molecules. The binding moiety may bind to an engineered tag on the target biomolecule. The binding moiety may be one half of a known tag/ligand pair, for example, biotin/avidin or GST/glutathione. The binding moiety may be a single-stranded polynucleotide complementary to a single-stranded polynucleotide target biomolecule. The binding moiety may be an antibody, antibody fragment, a bispecific antibody or other antibody-based molecule or compound designed to bind to a specific target biomolecule. The binding moiety may be the same type of molecule as the target biomolecule, for example, a target protein biomolecule may be bound by a peptide-based binding moiety. Single stranded polynucleotides of complementary sequence may hybridize to form double stranded polynucleotides. The binding moiety may be a different type of molecule from the target biomolecule, for example, a polynucleotide binding moiety may bind to a protein target biomolecule.

"Biomolecule" as used herein includes large macromolecules (or polyanions) such as proteins, carbohydrates, lipids, and nucleic acids, as well as small molecules such as primary metabolites, secondary metabolites, and nucleotides. The biomolecules may be isolated from a natural source or be synthetically produced.

"Buffer" as used herein means a solution capable of resisting changes in pH when other components, either acidic or alkaline, are added to the solution. Buffers typically include a weak acid or base together with one of its salts.

"Complement" or "complementary" as used herein means a nucleic acid is Watson-Crick (e.g., A-T/U and C-G) or Hoogsteen base paired with nucleotides or nucleotide analogs with the same or another nucleic acid molecule. "Complementarity" refers to a property shared between two nucleic acid sequences, such that when they are aligned antiparallel to each other, the nucleotide bases at each position will be complementary.

"Electrophoresis matrix" refers to the porous material used during electrophoresis that provides a torturous path through which analytes migrate in an electric field; effectively sieving the analytes through pores of different sizes. The matrix may also prevent convective currents of the buffer solution from disturbing the separation. Electrophoresis matrices are commonly formed from polymeric molecules, such as starch, agarose, and polyacrylamide, or paper.

"Fabric" refers to woven, non-woven, or felted fabrics. The fabric may be of any length and diameter, and may be hollow or solid. Non-woven fabrics are flat, porous sheets made directly from separate fibers bonded together by entangling fiber or filaments, thermally or chemically. Woven fabrics are produced by the interlacing of fibers in a regular pattern or weave style. Pore size can be chosen based on the number and size of fibers in a given area.

"As used herein, "gel" refers to material in which a dilute cross-linked system forms a porous network mostly comprised of a liquid. The cross-linked system is commonly formed from monomeric molecules including agarose, acrylamide, starch or any combination thereof which form cross-links to each other and give the gel its structure.

"Ion concentration polarization" or "ICP" is a phenomenon which occurs around an ion permselective membrane wherein ion concentration becomes polarized across the membrane. For example, in the case of cation selective membrane, when voltage is applied, the ion concentration would decrease around the anodic side of the membrane and increase around the cathodic side of the membrane. Those two regions are referred to as "ion depletion zone" and "ion enrichment zone", respectively. An "ion depletion front" forms when the voltage is reversed and is applied in the opposite direction of the initial electric field and ion depletion zone migrates away from the membrane. Just ahead of the ion depletion front an unusually high amount of ions accumulate because of a sharp electric field gradient between the high electric mobility environment in the ion depletion zone and the low electric mobility environment in the concentrated ion depletion front.

An "ion permselective membrane" is a membrane that allows the passage of selected ions, while substantially maintaining the integrity between the contents separated by the membrane. For example, a cation permselective membrane is negatively charged and will allow passage of cations but prevent the passage of anions or other molecules through the membrane. Conversely, an anion permselective membrane is positively charged and will allow the passage of anions while preventing the passage of cations through the membrane.

"Isotachophoresis" is a technique used for the separation and concentration of ionic analytes. Isotachophoresis is a variant of electrophoresis, generally carried out in a discontinuous buffer system. Sample material to be separated is inserted between a "leading electrolyte" and a "terminating electrolyte", the characteristic of these two buffers being that the leading electrolyte has to have ions of net mobility higher than those of sample ions, while the terminating electrolyte", must have ions of net mobilities lower than those of sample ions. In "depletion zone isotachophoresis" an ion depletion zone replaces the trailing electrolyte.

As used herein, "microfluidic" refers to a system or device having one or more fluidic channels, conduits or chambers that are generally fabricated at the millimeter to nanometer scale to allow a fluid to pass through.

As used herein, "channel" refers to a structure wherein a fluid may flow. A channel may be a capillary, a conduit, a strip of hydrophilic pattern on an otherwise hydrophobic surface wherein the contents, whether a fluid, or in the case of the present invention, an electrophoresis matrix, are confined to only within the channel. The "microfluidic channels" or alternatively referred to herein as "microchannels" of the present invention generally have cross-sectional dimensions ranging from about 1 mm or less.

"Mismatch" as used herein means that a nucleotide in one strand of DNA or RNA does not or cannot pair through Watson-Crick base pairing and it-stacking interactions with a nucleotide in an opposing complementary DNA or RNA strand. Thus, adenine in one strand of DNA or RNA would form a mismatch with adenine in an opposing complementary DNA or RNA strand. Mismatches also occur where a first nucleotide cannot pair with a second nucleotide in an opposing complementary DNA or RNA strand because the second nucleotide is absent (i.e., one or more nucleotides are inserted or deleted).

"Multimer" or "linked nanoparticle multimer" are used interchangeably herein to mean a complex of nanoparticles associated with each other through the binding of at least one target biomolecule with two different probes wherein the probes contain a binding moiety configured to bind the biomolecule and a nanoparticle. The multimer must contain at least two nanoparticles. For example, a single biomolecule binds two different probes and results in a dimer of nanoparticles. When the multimer contains three nanoparticles, two biomolecules may bind two different binding moieties of a single probe and then also bind two different binding moieties of two different probes, thereby causing the association of three different nanoparticles. This association can continue to form a chain or cluster of nanoparticles due to the ability of a single probe to bind a number of different target biomolecules.

"Nanoparticle" as used herein refers to a particle having dimensions of from 1 to 5000 nanometers, having any shape or morphology. Nanoparticles are classified based on their properties, shapes or sizes. Different classification groups based on their component materials include carbon-based nanoparticles, metal nanoparticles, ceramic nanoparticles, and polymeric nanoparticles. Nanoparticles also include quantum dots, up-conversion nanoparticles and fluorescent dielectric nanoparticles.

"Paper" as used herein refers to any good quality paper comprised of greater than 90% cellulose. For example, this can include both quantitative and qualitative filter paper as well as chromatography paper.

"Polynucleotide" or "oligonucleotide" or "nucleic acid" as used herein means at least two nucleotides covalently linked together. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. Polynucleotides may be single stranded or double stranded, or may contain portions of both double stranded and single stranded sequence. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The proteins may be modified by the addition of sugars, lipids or other moieties not included in the amino acid chain. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

A "probe" as used herein refers to a single nanoparticle coupled to a plurality of binding moieties. The nanoparticle and the binding moieties may be any of those described herein. A binding moiety may be coupled to the nanoparticle by any methods known in the art based on the type of binding moiety and the type of nanoparticle being utilized.

A "thread" as used herein means any natural or synthetic fiber. The thread may be of any length, diameter, and may be hollow or solid. The thread may be comprised of cotton or silk or some combination thereof. The thread can be chemically treated to adjust the hydrophilicity to either be more hydrophobic or more hydrophilic. The threads may be functionalized, such as conductive threads or nano-infused threads. The threads may be wax coated. The terms "thread" or "yarn" can be used interchangeably herein.

In the context of the present application, the terms "to separate" and "separation" are intended to mean any spatial partitioning of a mixture of two or more analytes based on their different behavior in an electrical field. Separation therefore includes, but is not limited to fractionation as well as to a specific and selective enrichment, depletion, concentration and/or isolation of certain fractions or analytes contained in a sample.

2. METHODS FOR SEPARATING BIOMOLECULES

Disclosed herein are methods for separating biomolecules. The methods comprise (a) providing a microfluidic device comprising a microchannel having a first end and a second end and containing an electrophoresis matrix, an ion permselective membrane in direct contact with the electrophoresis matrix, and first and second electrodes configured to apply an electric field across the ion permselective membrane, (b) loading a sample containing a plurality of biomolecules, a plurality of first probes and a plurality of second probes into the electrophoresis matrix, wherein each of the first probes comprises a first nanoparticle coupled to a plurality of first binding moieties, and each of the second probes comprises a second nanoparticle coupled to a plurality of second binding moieties, and wherein the first binding moieties and second binding moieties are configured to bind target biomolecules within the plurality of biomolecules, (c) applying a first electric field that causes the plurality of biomolecules, the plurality of first probes and the plurality of second probes to move through the electrophoresis matrix towards the ion permselective membrane whereupon the plurality of biomolecules, the plurality of first probes and the plurality of second probes become concentrated in the electrophoresis matrix adjacent to the ion permselective membrane, wherein at least some of the target biomolecules bind to one of the plurality of first probes and one of the plurality of second probes to form a plurality of linked nanoparticle multimers comprising at least one first nanoparticle and at least one second nanoparticle, and (d) applying a second electric field to form an ion depletion front as a result of ion concentration polarization, whereupon the ion depletion front moves away from the ion permselective membrane and whereupon linked nanoparticle multimers at the ion depletion front aggregate and precipitate and whereupon biomolecules, first probes and second probes not contained within a linked nanoparticle multimer move through the electrophoresis matrix away from the ion permselective membrane behind the ion depletion front.

a. Microfluidic Devices

The microfluidic devices comprise a microchannel having a first end and a second end and containing an electrophoresis matrix, an ion permselective membrane in direct contact with the electrophoresis matrix, and a first electrode and a second electrode configured to apply an electric field is applied across the ion permselective membrane i. Electrophoresis Matrices The microfluidic devices described herein comprise a microchannel having a first end and a second end and containing an electrophoresis matrix. In some embodiments, the electrophoresis matrix may comprise at least one of a gel, paper, fabric or thread.

Electrophoresis matrices are chosen based on the desired separation and the type and quantity of molecules being separated. A suitable matrix should be chemically inert to the analytes and allow resolution of the different sized molecules being separated. Various physical characteristics can be tailored for different separations depending on the type of matrix.

Exemplary gels may include, but are not limited to, agarose, acrylamide, starch or any combination thereof. Acrylamide gels, for example, may be linear acrylamide, polyacrylamide, polydimethylacrylamide, polydimethylacrylamide/coacrylic acid or a combination thereof. Starch gels, for example, may be methyl cellulose, polyethylene oxide, hydroxycellulose, hydroxy ethyl cellulose, or a combination thereof.

Various methods and agents known in the art may be chosen to provide a gel having a set of desired polymer properties for biomolecule separation such as (i) pore size; (ii) mechanical strength, which may be enhanced by using high polymer cross-linking density (using for example, 1% to 100% of polyfunctional acrylates such as pentaerythritol triacrylate, polyfunctional methacrylate, such as 1,3 butanediol dimethacrylate, or polyfunctional acrylamide, such as methylene bisacrylamide); (iii) hydrophobicity/hydrophilicity, which may be controlled through the choice of monomers, e.g., acrylamide, ethylene glycol diacrylate, or zwitterionic molecules, for hydrophilicity, and alkyl-acrylates for hydrophobicity; and (iv) polymer charge, which may be controlled through incorporation of charged monomers into the polymeric element, such as, for example, 2-(acryloyloxy)ethyl ammonium methyl sulfate salt (MOE) for positive charge, 2-acrylamido-2-methyl-1-propanesulfonic acid (AMPS) for negative charge.

The total concentration of agarose, polyacrylamide, starch or any combination thereof may be from about 0.1% to about 50% depending on the components being used to form the gel, the various properties desired and the biomolecules being separated. For example, a gel useful for the separation of polynucleotides or polypeptides may contain 0.1% to 10% agarose. Alternatively, an acrylamide gel may be between 4% and 20% polyacrylamide.

The gel may be in situ fabricated in microchips using any method known in the art. For example, the microchannel may be filled with a liquid solution comprising agarose, polyacrylamide, starch or any combination thereof. The solution may contain a photoinitiator, for example, riboflavin or methylene blue, whereby gel formation is initiated by UV-light. The solution may contain a source of free radicals that initiate polymerization of the gel, for example ammonium persulfate. The solution may be heated whereby gel formation occurs as the solution cools.

A paper electrophoresis matrix may include high quality cellulose-based paper, such as that found in qualitative and quantitative filter papers or chromatography papers. Many types of paper are available in various degrees of porosity and thickness. In general thick, coarse papers afford more rapid flow, and poorer resolution, than thinner more compact papers. The paper may be supported on a glass or other inert surface to provide strength and a barrier to diffusion of the molecules out of the paper matrix. In general, high quality papers with >90% cellulose may facilitate better resolution due to a more homogenous cellulose matrix.

A fabric electrophoresis matrix may include woven, non-woven, or felted fabrics. The fabric may be of any length and diameter necessary to fill the microchannel from the first end to the second end, and may be hollow or solid. Non-woven fabrics are flat, porous sheets made directly from separate fibers bonded together by entangling fiber or filaments, thermally or chemically. Typically, non-woven fabrics have from 1 to 500 micron mean flow pore (MFP) ratings. For non-woven and felted fabrics, entangled fibers create the porous structure. Woven fabrics are produced by the interlacing of fibers in a regular pattern or weave style. For woven fibers the spaces between the interlaced fibers create the porous structure. The porosity for fabrics can be chosen based on the number of fibers and the relative diameter of the fibers in a given area.

A thread electrophoresis matrix may contain one or more threads aligned parallel to each other along the microchannel. Threads can be derived from natural materials, such as cotton and silk, or can be made using synthetic biomaterials on a large scale using well-known spinning processes. Threads may be of any length and diameter necessary to fill the microchannel from the first end to the second end, and may be hollow or solid. The mechanical and degradation properties of threads can be modified by changing the material composition. For example, the thread can be chemically treated by methods know in the art to adjust the hydrophilicity to either be more hydrophobic or more hydrophilic. The threads may be functionalized, such as conductive threads or nano-infused threads. The threads may be wax coated.

A buffer may provide ions to maintain a relatively constant pH value and carry the electrical current through the electrophoresis matrix in the microchannel. Any buffers suitable for electrophoresis may be used with the microfluidic device and method described herein. Some of the more common electrophoresis buffers include Tris/Acetate/EDTA (TAE), Tris/Borate/EDTA (TBE) and Tris/Glycine. Buffer reservoirs may be located the first end and the second end of the microchannel containing the electrophoresis matrix.

ii. Ion Permselective Membranes

The microfluidic devices described herein comprise an ion permselective membrane in direct contact with the electrophoresis matrix. The ion permselective membrane may be cation selective or anion selective. For example, a cation permselective membrane is negatively charged and allows positive ions to pass through the membrane whereas negative ions are unable to pass through the membrane. Conversely, an anion permselective membrane is positively charged and allows negative ions to pass through whereas cations are excluded. The charge of ion permselective membrane should match the charge of the biomolecules being separated. For example, if the biomolecules are negatively charged nucleic acids, the membrane should be negatively charged cation selective membrane. If the biomolecules are positively charged proteins, the membrane should be positively charged anion selective membrane.

Any commercially available ion permselective membrane may be used. For example, the ion permselective membrane may comprise polytetrafluoroethylenes (PTFEs), perfluorosulfonates, polyphosphazenes, polybenzimidazoles (PBIs), poly-zirconia, polyethyleneimine-poly(acrylic acid), poly (ethylene oxide)-poly(acrylic acid), non-fluorinated hydrocarbon polymers, polymer-inorganic composites, organosulfonates or sulfonated tetrafluorethylene copolymer. The sulfonated tetrafluorethylene copolymer may comprise Nafion solution.

One side or both sides of the ion permselective membrane may be in direct contact with the electrophoresis matrix. If only a single side of the ion permselective membrane is in contact with the electrophoresis matrix, a reservoir containing a buffer may be immediately adjacent to and in contact with the other side of the ion permselective membrane.

iii. Electrodes

The microfluidic devices described herein further comprise a first electrode and a second electrode configured to apply an electric field across the ion permselective membrane. The electrodes may be located on either side of the ion permselective membrane. The electrodes may be in direct contact with the electrophoresis matrix or in a buffer reservoir located at either end of the electrophoresis matrix or adjacent to the ion permselective membrane. The electric field may be induced by applying a voltage or a current across the two electrodes. The current or voltage may be applied unequally between the two electrodes.

b. Loading a Sample into the Microfluidic Device

The methods described herein comprise loading a sample containing a plurality of biomolecules, a plurality of first probes and a plurality of second probes into the electrophoresis matrix, wherein each of the first probes comprises a first nanoparticle coupled to a plurality of first binding moieties, and each of the second probes comprises a second nanoparticle coupled to a plurality of second binding moieties, and wherein the first binding moieties and second binding moieties are configured to bind target biomolecules within the plurality of biomolecules.

The sample may be loaded within or on top of the electrophoresis matrix. For example, when the electrophoresis matrix is a gel, a section of the gel may be removed to create a well or cavity wherein the liquid sample fills the well. For a paper or fabric electrophoresis matrix, a liquid sample may be applied on the top surface, wherein the matrix absorbs the sample.

i. Biomolecules

The plurality of biomolecules may be selected from the group consisting of polynucleotides, polypeptides, proteins or various combinations thereof. The biomolecules may be natural or synthetic.

Polynucleotides may comprise of DNA, RNA or a combination of DNA and RNA. The polynucleotides may be single stranded, double stranded. Double stranded polynucleotides are those in which all the bases are paired with a complementary base on a second polynucleotide strand. For example, some of the single stranded polynucleotides may comprise a sequence complementary to other single stranded polynucleotides. The polynucleotides may also have a combination of single and double stranded portions wherein only a subset of the bases are engaged in complementary base-pairing.

The polynucleotides may comprise of 10 to 1000 nucleotides. For example, the polynucleotides may comprise 10 to 50 nucleotides, 10 to 100 nucleotides, 10 to 250 nucleotides, 10 to 500 nucleotides, 100 to 1000 nucleotides, 250 to 1000 nucleotides, or 500 to 1000 nucleotides.

ii. Probes

The sample also includes a plurality of first probes and a plurality of second probes, wherein each of the first probes comprises a first nanoparticle coupled to a plurality of first binding moieties, and each of the second probes comprises a second nanoparticle coupled to a plurality of second binding moieties.

The plurality of first binding moieties and the plurality of second binding moieties are independently selected from polynucleotides, polypeptides, proteins and small organic molecules. The binding moieties may be natural or synthetic.

The polynucleotides may comprise of DNA, RNA or a combination of DNA and RNA. The polynucleotides may be single stranded, double stranded. Double stranded polynucleotides are those in which all the bases are paired with a complementary base on a second polynucleotide strand. For example, some of the single stranded polynucleotides may comprise a sequence complementary to other single stranded polynucleotides. The polynucleotides may also have a combination of single and double stranded portions wherein only a subset of the bases are engaged in complementary base-pairing.

The polynucleotides may comprise of 10 to 1000 nucleotides. For example, the polynucleotides may comprise 10 to 50 nucleotides, 10 to 100 nucleotides, 10 to 250 nucleotides, 10 to 500 nucleotides, 100 to 1000 nucleotides, 250 to 1000 nucleotides, or 500 to 1000 nucleotides.

The first binding moieties and second binding moieties are configured to bind target biomolecules. The first binding moieties and second binding moieties may bind to different locations on the same target biomolecule, thereby allowing a single target biomolecule to bind both a first binding moiety and a second binding moiety. The binding moiety may be the same type of molecule as the target biomolecule, for example, a target protein biomolecule may be bound by a peptide-based binding moiety. Single stranded polynucleotides of complementary sequence may hybridize to form double stranded polynucleotides. The binding moiety may be a different type of molecule from the target biomolecule, for example, a polynucleotide binding moiety may bind to a protein target biomolecule.

The first binding moiety and the second binding moiety may bind to the same target molecule by a similar mechanism. For example, the first binding moiety and the second binding moiety may be two different single stranded polynucleotides that bind to a single stranded target biomolecule at two different sequences. The first binding moiety and the second binding moiety may bind to the target molecule with a different association. For example, the first binding moiety may be a double stranded polynucleotide and the second binding moiety may be an antibody that binds to different location within a protein target biomolecule.

Each of the plurality of first binding moieties and the plurality of second biomolecules is coupled to a nanoparticle. Any type of nanoparticle may be utilized for coupling to the binding moieties. The nanoparticle may be a metal nanoparticle, a quantum dot, and up-conversion nanoparticle or a fluorescent dielectric nanoparticle. Exemplary metal nanoparticles may comprise a metal selected from the group consisting of gold, silver, copper, aluminum, chromium or an alloy or combination thereof. The metal nanoparticle may be comprised of gold.

The nanoparticles may have various shapes such as a sphere, square, rod, or prism. The nanoparticles may be between 1 and 500 nm in diameter. For example, the nanoparticles may be between 1 and 500 nm in diameter, between 1 and 400 nm in diameter, between 1 and 300 nm in diameter, between 1 and 200 nm in diameter, between 1 and 100 nm in diameter, between 1 and 50 nm in diameter, between 50 and 500 nm in diameter, between 100 and 500 nm in diameter, between 200 and 500 nm in diameter, between 300 and 500 nm in diameter, or between 400 and 500 nm in diameter.

The first nanoparticle and the second nanoparticle may be an identical type of nanoparticle. The first nanoparticle and the second nanoparticle may be two different types of nanoparticles.

Any particular method known in the art may be used to couple the binding moiety to the nanoparticle. The coupling method will depend on the type of binding moiety and nanoparticle being utilized. Binding reagents that are at least bifunctional, having at least one functionality directed to binding moiety binding and another functionality directed to binding to the surface of the nanoparticle, may be used to facilitate coupling. For example, oligonucleotides may be functionalized with alkanethiols at the 3' or 5' termini which allows attachment to a various metal nanoparticles. Proteins may use bifunctional binding reagents where one end is linked to the nanoparticle and the other is linked to an exposed amine group, for example, with the use of N-hydroxysuccinimide (NHS)-containing reagents. Other functional groups for attaching binding moiety to nanoparticles include phosphorothioate groups, substituted alkylsiloxanes, disulfides or cyclic disulfides, and carboxylic acids. In some cases, functionalities for coupling a binding moiety to a nanoparticle may inherently reside in the binding moiety itself, such as in amino acid side chain of a protein or polypeptide-based binding moiety.

The nanoparticles may be comprised of gold and the binding moieties may be polynucleotides. For this combination, the polynucleotides may be modified to include a thiol group. The sulfur of the thiol group may covalently bind to the gold nanoparticle. The thiol group may require reduction prior to binding the gold nanoparticle.

The binding moieties may be purified prior to coupling. For example, binding moieties modified with a coupling reagent may be purified using spin column purification. The assay platform may also be readily integrated with gel systems such as those which purify biomolecules from large cell lysate debris or more complex samples.

c. Applying a First Electric Field

The methods described herein comprise applying a first electric field that causes the plurality of biomolecules, the plurality of first probes and the plurality of second probes to move through the electrophoresis matrix towards the ion permselective membrane whereupon the plurality of biomolecules, the plurality of first probes and the plurality of second probes become concentrated in the electrophoresis matrix adjacent to the ion permselective membrane, wherein at least some of the target biomolecules bind to one of the plurality of first probes and one of the plurality of second probes to form a plurality of linked nanoparticle multimers comprising at least one first nanoparticle and at least one second nanoparticle.

The first electric field may be applied at constant voltage. The first electric field may be applied at between about 5 volts and about 500 volts. The first electric field may be applied at between about 5 volts and about 50 volts, between about 5 volts and about 100 volts, between about 5 volts and about 200 volts, between about 5 volts and about 300 volts, between about 5 volts and about 400 volts, between about 50 volts and about 100 volts, between about 50 volts and about 200 volts, between about 50 volts and about 300 volts, between about 50 volts and about 400 volts, between about 50 volts and about 500 volts, between about 100 volts and about 200 volts, between about 100 volts and about 300 volts, between about 100 volts and about 400 volts, between about 100 volts and about 500 volts, between about 200 volts and about 300 volts, between about 200 volts and about 400 volts, between about 200 volts and about 500 volts, between about 300 volts and about 400 volts, between about 300 volts and about 500 volts, or between about 400 volts and about 500 volts.

Due to the selectivity of the permselective membrane the plurality of biomolecules, the plurality of first probes and the plurality of second probes concentrate in the electrophoresis matrix adjacent to the ion permselective membrane. The electric field may be applied for a length of time necessary to cause all of the biomolecules, the plurality of first probes and the plurality of second probes to move through the electrophoresis matrix and concentrate in the electrophoresis matrix adjacent to the ion permselective membrane. The electric field may be applied for a longer length of time than necessary to cause all of the biomolecules, the plurality of first probes and the plurality of second probes to move through the electrophoresis matrix and concentrate in the electrophoresis matrix adjacent to the ion permselective membrane.

Upon concentration at least some of the target biomolecules may bind a first binding moiety coupled to a first nanoparticle and a second binding moiety coupled to a second nanoparticle to form a plurality of linked nanoparticle multimers comprising at least one first nanoparticle and at least one second nanoparticle. If a single probe binds more than one biomolecule, a linked nanoparticle multimer may contain more than one first nanoparticle and/or more than one second nanoparticle Single stranded polynucleotide target biomolecules may comprise a sequence complementary to single stranded polynucleotides of the first binding moiety and single stranded polynucleotides the second binding moiety. These single stranded polynucleotides may hybridize to form double stranded polynucleotides. The double stranded polynucleotides may comprise base pair mismatches. The double stranded polynucleotides may comprise less than three base pair mismatches. For example, the double stranded polynucleotides may comprise one, two, or three base pair mismatches. The double stranded polynucleotides may comprise zero base pair mismatches. The base pair mismatches may be located anywhere along the complementary polynucleotide strand. The base pair mismatches may be in the middle of the complementary polynucleotide strand or at the end of the complementary polynucleotide strand. The base pair mismatches may or may not be adjacent to another base pair mismatch.

The application of the first electric field across the ion permselective membrane results in ion concentration polarization (ICP). ICP refers to an electrochemical transport phenomenon wherein ion concentration becomes polarized across a membrane. For example, when voltage is applied across a cation selective membrane, anions accumulate at the surface of the membrane because fixed negative charges prevented any negatively charge entity from passing through. However, cations pass through freely leading to an enrichment of ions on one side of the membrane, referred to as an "ion enrichment zone".

d. Applying a Second Electric Field

The methods described herein comprise applying a second electric field to form an ion depletion front as a result of ion concentration polarization, whereupon the ion depletion front moves away from the ion permselective membrane and whereupon linked nanoparticle multimers at the ion depletion front aggregate and precipitate and whereupon biomolecules, first probes and second probes not contained within a linked nanoparticle multimer move through the electrophoresis matrix away from the ion permselective membrane behind the ion depletion front.

The second electric field may be applied in a direction opposite to that of the first electric field. When the electric field is reversed, both cations and anions migrate away from the ion permselective membrane leaving behind a zone depleted of ions, referred to as an "ion depletion zone". Because the system maintains electroneutrality, cations encounter the anions at the head of the depletion region and form a concentrated ion depletion front.

As the ion depletion front moves away from the ion permselective membrane, linked nanoparticle multimers at the ion depletion front precipitate aggregate and precipitate. Biomolecules, first probes and second probes not contained within a linked nanoparticle multimer move away from the ion permselective membrane behind the ion depletion front and are separated from the linked nanoparticle multimers.

The second electric field may be applied at a constant voltage. The second electric field may be decreased over time. The second electric field may be decreased linearly or stepwise. The second electric field may be applied continuously.

e. Quantification

The methods described herein further comprise quantifying the precipitated linked nanoparticle multimers. The linked nanoparticle multimers may be quantified with any known method for measuring the intensity of light absorption or emission of the nanoparticles. The choice of measurements will depend on the type of nanoparticle. Ultraviolet-visible (UV-Vis), plasmonic absorption/emission, photoluminescence and fluorescence are the well-known optical techniques which may be used to detect and quantify nanoparticles. For example, nanoparticles comprising alkali and noble metals (Cu, Ag and Au) have a broad absorption band in the visible zone of the electromagnetic solar spectrum and can be easily visualized and/or photographed without any special equipment. Fluorescence or visible absorption images can be quantified using standard pixel intensity software, such as ImageJ. Once a measurement of the intensity of the light absorption or emission is known, a comparison to a standard curve may provide quantification of the sample.

3. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1

Materials:

Fluorescein sodium salt was obtained from Fisher Scientific. Sodium chloride, sodium citrate and chloroauric acid trihydrate were obtained from Sigma-Aldrich. SYBR green I was received at 10,000× concentration from Invitrogen. Buffers were prepared by dilution from 10×PBS (pH 7.4) and 50×TAE (pH 8.4) obtained from Boston Bioproducts and 150 mM sodium phosphate buffer (pH 7.2) obtained from Teknova. Agarose gels were prepared at 1 wt % in 1×TAE using agarose powder from Ominpur and stored as liquids inside an oven maintained at 65° C. All agarose gels containing fluorescein were prepared in a like manner with the fluorescein concentration equal to 10 mM. QuikCast polyurethane casting resins (side A and side B) were obtained from TAP Plastics Inc. Acrifix 1R 0192 UV reactive cement was obtained from Evonik Industries while Loctite 3492 light cure adhesive was obtained from Loctite Corporation. RALEX cation-exchange membranes whose fixed negative charge is supplied by organosulfonate groups were provided by Mega a.s (CzechRepublic).

Custom single stranded DNA probes and target sequences were used as received from Integrated DNA Technologies Inc. The DNA probes and nontarget were dissolved in water to concentrations of 1 mM while the target DNA were dissolved in water to concentrations of 0.1 mM. All DNA samples were stored in a freezer at −4° C. until ready for use. The probes were prepared for use by dissolution at 0.1 mM in a 1×TE buffer (pH 8.0) containing 10 mM DL-dithiothreitol (DTT). The DTT was used to reduce the thiol modifiers from their oxidized form by reacting at room temperature for two hours. After the reaction was complete, the solution was purified from the DTT by running it through a Roche mini Quick Spin DNA column. Concentrations were determined from absorbance measurements on a Thermo Scientific NanoDrop 2000 spectrophotometer using the 260 nm peak. Although it possible to functionalize DNA onto gold nanoparticles with DTT reduction and spin column purification, these two steps were found critical to improving the performance of the assay in terms of selectivity.

Synthesis and Functionalization of Gold Nanoparticles:

Gold nanoparticles with mean diameter 20 nm were provided by nanoComposix, Inc. Gold nanoparticles were prepared by standard citrate reduction. They were sized by a Malvern Nano-ZS Zetasizer and found to be approximately 20-30 nm in diameter. Their concentration was 2 nM as determined by UV-Vis spectroscopy using a Thermo Scientific NanoDrop 2000 spectrophotometer. The particles were functionalized with DNA probes, in separate solutions, by gold-thiol bonding. The final nanoparticle concentration was approximately 8 nM. DNA target solutions from 1 mM down to 10 pM were prepared by mixing equal amounts of probe 1 and 2 nanoparticles followed by adding DNA targets. A nontarget solution was prepared in a like manner at 10 mM. Heterogeneous mixtures were also prepared with concentrations of 1 nM target/10 mM nontarget and 100 pM target/1 mM nontarget. The solutions were mixed vigorously and incubated for at least twelve hours before use.

Chip Fabrication:

Microfluidic chips were fabricated from 300 mm polycarbonate sheets in a layer-by-layer fashion forming a single, straight channel with dimensions 2 mm width×60 mm length×500 mm height. At either end of the channel were inlet/outlet holes for fluid and liquid gel. A 2 mm×2 mm square hole for inserting the sample lay 10 mm from the inlet and between the inlet and the membrane. Another 6.9 mm diameter hole whose center was 10 mm away from the sample hole held the membrane cast. The cation-exchange membrane was sealed to the bottom of the cast and remained flush with the top of the microfluidic channel. The chip schematic, as detailed above, is shown in FIG. 1C.

In some examples the chip had four channels, 2 mm width×15 mm length×500 µm height, which intersected in the center of the chip. Fluid inlets were set at the ends of the channel. Each channel was bisected by a 10 mm long cross-channel for the sample inlet. A 6.9 mm diameter hole was placed in the center of the chip to hold the membrane cast. A 4 mm×4 mm cation-exchange membrane was sealed to the bottom of the cast and remained flush with the top of the microfluidic channel. The chip, as detailed above, is shown in FIG. 7E.

Example 2

Separation and Detection Protocol:

Chips, as shown in FIG. 1C, were filled with agarose gel and used after the gel solidified. The gel occupying the sample reservoir was removed and filled with 2 mL nanoparticle/DNA sample. The fluid reservoirs were all filled with 1×TAE buffer. Gel electrophoresis was conducted using a Keithley 2400A Sourcemeter with platinum electrodes as the voltage source. This example protocol consisted of four steps: enrichment, depletion, expulsion, and repacking. First, during enrichment, shown in FIG. 1A, the positive electrode was placed inside the membrane reservoir while the ground electrode was placed inside the inlet reservoir, and the sample was electrophoretically driven towards the membrane for five minutes by a 150V potential. The particles required approximately one minute to reach the membrane at which point the sample reservoir was refilled with agarose gel. Second, during depletion, typically eight to nine minutes, the field was reversed by changing the electrode potential in the membrane reservoir to −150V. As shown in FIG. 1B, this generated a depletion front causing aggregation of one fraction of the nanoparticles while forcing away the remainder back towards the sample loading reservoir. Third, expulsion was conducted by transferring the electrode in the membrane reservoir to the sample reservoir for one minute and forcing the particles therein into the region between the sample and inlet reservoirs. Fourth, in the repacking step, the field was reversed again with the positive electrode at 150V in the membrane reservoir and the ground in the sample reservoir. The aggregated nanoparticles were concentrated and repacked against the membrane. From sample loading to target detection, the total time required was sixteen minutes.

The nanoparticles were imaged using a QImaging Retiga 2000R Fast 1394 camera and custom MATLAB programming. Images were recorded before the enrichment and depletion steps and after the repacking step. The particles near the membrane were quantified using the mean pixel intensity as measured by ImageJ. The fraction of aggregated particles was then calculated by taking the ratio of the intensity after repacking to the intensity after enrichment.

Hybrid Membrane-Gel Electrophoresis:

Ion concentration polarization by the cation-exchange membrane is an essential feature of this new detection strategy. A positive potential applied above the membrane electrophoretically drove anions and negatively charged gold particles to accumulate at the surface because fixed negative charges prevented any negatively charged entity from passing through due to electrostatic repulsion. On the other hand, cations passed through freely leading to an enrichment effect beneath the membrane surface as in FIG. 1A. When the applied potential became negative, both cations and anions migrated away from the enriched region leaving behind a zone depleted of ions. Because the system must maintain electroneutrality, cations encountered the anions at the head of the depletion region and formed the concentrated ion front illustrated in FIG. 1B. High voltages tend to produce an extended space-charge region which forms a vortex instability that mixes the bulk electrolyte with the depletion zone and increases the current. In this system however, the gel suppressed vortex formation.

A fluorescein doped gel showed that the depletion region migrated down the channel creating a sharp boundary between the depletion region and the ion. The depletion was monitored by tracking the movement of the bright green fluorescein ions next to the dark, depleted region. The current fells dramatically due to lack of charge carriers in the depletion region. The drop in current placed a high-field and a low-field region adjacent to each other and therefore facilitated an isotachophoretic separation front and avoided the tedious task of loading the channel with two different conductivity buffers. As discussed herein, this isotachophoretic front was responsible for the selective aggregation of DNA-linked nanoparticles.

A combination of probe-functionalized gold nanoparticles, cation-exchange membranes, and gel electrophoresis were used to isolate and detect specific DNA sequences. The two probe sequences were 5'/TGG TTC TCT CCG AAA TAG CTT TAG GG TA/3' (SEQ ID NO: 1) for probe 1 and 5'/GAA GGG AAG AGG AAG AGG CAG GTG TCC TGT GGT AG/3' (SEQ ID NO: 2) for probe 2. Probe 1 possessed a thiol modification at the 5' end while probe 2 possessed a thiol modification at the 3' end. The target sequence was 5'/CT ACC ACA GGA CAC CTG CCT CTT CCT CTT CCC TTC AAAAA TA GCC CTA AAG CTA TTT CGG AGA GAA CCA/3' (SEQ ID NO: 3) while the nontarget sequence was 5'/GCT GGC ACT CTA CAC TAG AAG GGA TAG ATA TGC CAA AAA AAC CAA ATT TCA GGC CCG GAA CTT TCT TGC/3' (SEQ ID NO: 4). An example separation of 100 nM target is illustrated in FIGS. 2A-D. In FIG. 2A, the nanoparticles packed at the membrane surface during enrichment. In FIG. 2C, the depletion caused the linked particles to aggregate whereas the uncaptured particles continued their migration back up the channel. As mentioned above, the expulsion and repacking steps were performed as in FIG. 2D which was necessary at low concentrations to enhance sensitivity and increase signal strength. There was a clear separation between targets and unlinked particles in less than 5 mm of channel length and less than seventeen minutes between sample loading and detection. The nanoparticle signal was isolated by image subtraction and set a threshold to avoid measurement noise. This assay was able to detect down to 10 pM or approximately 10 million copies with the sample volume. The result was comparable to previous isotachophoretic platforms with gel filters that reported detection of 300 million copies of miRNA. Electrochemical methods such as differential pulse voltammetry have reported detection limits that vary from 800 pM to 2 pM down to 0.4 fM and 0.2 fM. Although these biosensors reported lower limits of detection, they typically relied on diffusion-based hybridization. Hence, they reported assay times from one hour up to five hours, particularly at low concentrations. In contrast, the assay described herein required less than twenty minutes from sample loading to detection. In addition, electrochemical sensors employ expensive fabrication methods and tedious preparation of electrodes making them unsuitable for point-of-care applications.

Following the procedure described above, the calibration curve shown in FIG. 3 was established for the 10 pM to 10 nM range. The system was highly selective between targets and nontargets. It should be noted that there was a small amount of aggregation despite the absence of any DNA targets or nontargets, and this was the baseline signal of the assay platform, yet down to 10 pM target above the baseline can be detected. On the other hand, even at 10 mM, the signal from the nontarget was, within error, equivalent to the baseline. Furthermore, the signal intensity in heterogeneous mixtures was maintained where the nontargets outnumber the targets by a factor of 10,000 to 1. At 1 nM and 100 pM, the mixture's signal was identical to the signal from pure target thereby demonstrating the selective nature of the assay and its potential use for complex media. The graph indicated two linear regimes: one from 100 pM to 1 nM and one from 1 nM to 8 nM with correlation coefficients of 0.96 and 0.98, respectively, for the lines of best fit. The ratio of nanoparticles to target molecules explained the presence of these two regimes and the decrease in sensitivity between 1 and 8 nM. In an ideal scenario, each target would link a nanoparticle to only one other nanoparticle and form them into dimers. However, in practice, targets linked nanoparticles into trimers, tetramers, and higher multimers. At low target concentrations, when the ratio of nanoparticles to targets is large, the probability to form dimers was much higher. At a concentration of 8 nM gold nanoparticles, the nanoparticle to target ratio went from 800:1 to 8:1 in the 100 pM to 1 nM range, respectively, and was significant enough to form mainly dimers. Above 1 nM, the ratio approached and then fell below 1:1 so that multimer formation became more probable. The concentration range where dimers form was more sensitive because each additional target corresponds to an additional two nanoparticles. In contrast, in the multimer regime there was a greater probability that targets would hybridize to particles already linked as dimers. Therefore, there was a smaller increase in the signal and consequently lower sensitivity. The changing sensitivity with the nanoparticle to target ratio demonstrated the scalability of the assay. The limit of detection can be potentially lowered by decreasing the concentration of the nanoparticles at low target concentrations to obtain higher order multimers and hence more severe aggregation. It follows that the dynamic range may also be increased by careful adjustment of the nanoparticle concentration depending on the amount of target present in the sample. This could be achieved by testing multiple channels with different nanoparticle concentrations simultaneously and then running subsequent measurements at only one concentration for greater precision.

Example 3

The selectivity of the sensor using targets with two base mismatches on each probe was examined (FIG. 4). The target sequence became 5'/CTACC<u>GT</u>AGGACACCTG CCTCTTCCTCTTCCCTTCAAAAATAGCCCTAAAGCT ATTTCGG <u>GC</u>AACCA/3' (SEQ ID NO: 6). The experiments were carried out using slightly altered conditions where the distance between the channel inlet and membrane reservoirs was reduced to 15 mm, the enrichment time was increased to six minutes, and the applied potential during depletion underwent a step change. The maximum output of the sourcemeter, −200 V, was applied for one minute, and then the potential was lowered for the remainder of the depletion step (i.e. until the monomer reached the sample reservoir). The greatest selectivity occurred when the potential was lowered to 100 V and the target to mismatch signal ratio was greater than 3 (FIG. 4). These results were comparable to other assays such as the NanoBioArray chip based on hybridization of target-conjugated nanoparticles to surface-immobilized probes and the molecular beacon/Ag nanocluster technique which reported selectivity values of approximately 3 to 6 and 2 to 3, respectively. It is important to note that the mismatches were in the middle of the probes rather than at the ends. Mismatches positioned in the middle may have significantly reduced the selectivity, yet the assay was able to discriminate between them and the completely matched target. Changing the electric field strength was important to improving the selectivity.

Example 4

In order to confirm the state of aggregation of the nanoparticles, SEM images of the two different bands were collected. To carry out the collection, a special chip was used where clear packaging tape replaced the bottom surface. After the depletion step separated the nanoparticles, the tape was peeled off, the two bands were cut from the gel, and then they were placed into separate containers in 20 mL of water. The solutions were heated at 60° C. for twenty minutes to melt the gel. The solutions were then dispensed onto silicon substrates and evaporated. Following evaporation, the substrates were washed with water to remove any residual salt. The dried particles were imaged by a Carl Zeiss EVO-50 SEM. The subsequent images were analyzed in ImageJ using the "Analyze Particles" function to determine the area of the particles from which the diameter was then calculated.

The SEM analysis confirmed the presence of monomers and multimers in the separated bands. The SEM image of the monomer band showed the dominant presence of monomer particles over dimers and higher multimers (FIG. 5A). The histogram analysis of the diameters of over 1000 particles (FIG. 5A, inset) indicated that the average particle diameter was 17 nm which corresponded well with the known diameters of the gold nanoparticles from dynamic light scattering. Very few particles possessed diameters above 30 nm which would have been indicative of the formation of dimers. Large aggregates dominated over the presence of monomers in the aggregated band (FIG. 5B). Although the histogram (FIG. 5B, inset) still showed some monomer particles, the distributions shifted significantly to higher diameters compared to the histogram for the monomer band (FIG. 5A, inset). The diameters of the aggregates may also have been underestimated due to the decreased circularity of the large aggregates. Moreover, during sample preparation, the heating stage which melted the gel may have denatured some of the hybridized pairs causing particle dissociation and thus resulting in more monomers. However, FIGS. 5A-B clearly proved that the depletion front aggregated linked particles but removed monomer particles.

Example 5

Further experiments examined the role of enrichment in the assay by investigating how the enrichment time affected aggregation. For an 8 nM target sample, the enrichment step was carried out for various times from one minute to twelve minutes, in one minute intervals. The subsequent depletion, expulsion, and repacking steps were performed as described above, although the time required for the depletion step was increased as the enrichment time increased. Overall, the fraction of aggregated particles increased linearly with the enrichment time although the data at one and two minutes fell below the baseline signal. Longer than six minutes, the slope decreased and finally saturation began at twelve minutes.

Other than reducing the diffusion time for nanoparticle linkages by concentrating the nanoparticles, the enrichment step also favorably affected the hybridization thermodynamics. Increasing numbers of targets hybridized to the nanoparticles while packing near the membrane surface. This effect can be explained by examining the thermodynamic equilibrium surrounding the hybridization reaction. The hybridization of a DNA target to a surface-bound probe can be written as T+P+JC→D where T is the target, P is the probe, and D is the hybridized duplex. The JC term accounts for a number, J, of cations, C, which are initially free in solution but associate to the duplex to screen the increased charge density on the DNA duplex. The equilibrium expression is then $$\frac{[D]}{[T][P][C]^J} = \frac{1}{K_D}$$

where $K_D$ is the dissociation constant.

Because target molecules and cations are small compared to the size of the nanoparticles, the expectation was that they would concentrate more than the nanoparticles which, by the surface bound nature of the probes, effectively provided a control of the probe and duplex concentrations. Therefore, the concentrations of targets and cations would increase relative to the concentration of the duplexes and push equilibrium to favor hybridization. When the field was reversed and the depletion formed, it was expected that the reverse reaction rate would increase. That is, the dissociation of duplexes as targets and cations would migrate away from the membrane. However, the depletion induced aggregation of the nanoparticles before significant dissociation. So, although dehybridization was thermodynamically more favorable during depletion, it was kinetically limited because of the aggregation. The dissociation constant was effectively lowered by the combined effects of enrichment and depletion. This result was particularly encouraging since target hybridization to surface-based probes tends to be less favorable than solution-based probes.

Further proof that hybridization took place during the enrichment step was determined by comparing the aggregation between targets hybridized on-chip and targets hybridized off-chip. For on-chip hybridization, 100 nM target samples were prepared, vortexed briefly, and then immediately analyzed using the assay protocol. For off-chip hybridization, normal samples were used with twelve hour hybridization. The aggregation was also compared to a 10 mM nontarget sample hybridized on-chip and samples with no target. The fractional aggregation for on-chip hybridization was identical to that for off-chip hybridization disposing of the need for the hours-long incubation step. Additionally, there was no significant aggregation from the nontarget DNA sample, so no selectivity was lost. Therefore, rapid, selective hybridization can be achieved on-chip and significantly reduced the total analysis time to less than twenty minutes. The enrichment concentrated the target which increased the reaction rate and thereby overcame the kinetic limitations and the transport-limited hybridization reaction in the bulk.

Example 6

The depletion front induced nanoparticle aggregation only for linked nanoparticles (FIG. 3 and FIGS. 5A & 5B). Field-induced nanoparticle dipoles were known to induce aggregation, but it was unclear why only linked particles aggregated in this assay. To elucidate the mechanism behind this curious selective aggregation, another experiment used a fluorescein doped gel to track the movement of the depletion region and simultaneously monitored the aggregation and separation of the nanoparticles. The separation did not take place until the depletion region reached the nanoparticles; after the separation, the monomers remained isotachophoretically packed against the depletion front and carried by the front downstream. This experiment was repeated with a series of pauses during the depletion step. Images (FIGS. 6A-F) simultaneously displayed the fluorescence-tracked depletion and the nanoparticles while the nanoparticles' position was confirmed by bright field images (not shown). FIG. 6A shows the nanoparticles' initial position at the beginning of the depletion step while FIG. 6B shows them three minutes later just as the depletion front begins to form. At this point, the first pause was introduced before any separation. Each pause lasted fifteen minutes, and during this time, the fluorescein diffused into the depletion region as in FIG. 6C. The voltage was reapplied for one minute and then was followed by another fifteen minute pause. When the voltage was reapplied, the depletion region quickly reformed, and overtook the nanoparticles (FIG. 6D). The fluorescein again diffused into the depletion region (FIG. 6E) until the voltage was applied for another minute to yield the final image, FIG. 6F, where the gap between the nanoparticles and the depletion front was very obvious. First, the nanoparticles no longer migrated under the applied field which indicated aggregation. Second, no separation existed between hybridized and unhybridized nanoparticles, which indicated the aggregation of both monomer (unhybridized) and multimer (hybridized) particles.

Results obtained from FIG. 6A-F revealed the role of depletion ramping in inducing selective aggregation, which can be explained by depletion induced isotachophoretic separation. Formation of the depletion region caused a rapid drop in current which in turn created a high electric field. At the same time, ions accumulated just ahead of the depletion front. A very sharp electric field gradient developed between the high electric mobility environment in the depletion region and the low electric mobility environment in the concentrated ion front. The adjacent high and low electric mobility environments facilitated the proper conditions for an isotachophoretic separation without using immiscible solvents with different ionic strengths. The linked and unlinked nanoparticles possessed enough of a mobility difference to separate within the isotachophoretic region. However, such a separation was feasible only with a continuous depletion front with all the nanoparticles initially packed at the membrane. The fluorescein ions were quite obviously diffuse into the depletion region. Although it was not readily apparent, the monomer and dimer particles were also potentially able to diffuse and mix with each other. Once the voltage was reapplied, however, the particles did not have enough time to separate before the depletion overtook them. Therefore, when the dimer particles aggregated, the monomer particles became trapped within the aggregated complex as well. When the depletion was run continuously instead, aggregation of only the linked particles was seen. With a continuous depletion front, the band of separated, linked dimers was in the high field region at the isotachophoretic front and the band of unlinked nanoparticles was in the high ionic strength, low field region just ahead. The large field gradient within the isotachophoretic front hence induced selective aggregation of the linked nanoparticles in the back of the front and not the unlinked nanoparticles at the front if the two sets of particles were separated at the isotachophoretic front with continuous depletion.

The dimerization of the particles in the advancing depletion front was shown to occur if the particles were linked by a single target molecule. This was due to a selective and irreversible aggregation kinetic mechanism in the presence of a decaying electric field. Recently, extensive characterization was performed of the interparticle interactions between Au nanoparticles functionalized with negatively charged ligands using an extended DLVO theory. The dominant interactions between the particles were the repulsive electrostatic forces and the attractive van der Waals (vdW) forces. The smaller particles (<50 nm), as used in this assay, had higher Hamaker constants. For conditions where spontaneous aggregation did not occur, a potential barrier more than 10 $k_B T$ existed at roughly a few nanometers of particle separation due to a balance between these two opposing interactions but both interactions vanished at more than 10 nm away. The linking target molecule reduced this barrier because of the preferred association of free polyvalent cations around the duplex that screened the electrostatic repulsion between the negatively charged particles. This aggregation barrier could be lowered significantly or even eliminated entirely by imposing a sufficiently high electric field due to an attractive interaction between the two induced nanoparticle dipoles. How much the barrier was lowered by the electric field can be estimated by the voltage drop across the separation where the barrier lies (a few nanometers). Most of the 150 V voltage drop was in the depleted region and hence when the depletion front had only advanced a few millimeters, the voltage drop across the barrier separation of a few nanometers would have been as large as 10 $k_B T$ but it would have decayed to below 1 $k_B T$ when the front advanced more than 1 cm. The barrier for linked particles hence disappeared and appeared in less than one minute between the time the depletion region hit the particles and the time it passed them. The particles would have aggregated spontaneously without the barrier because the linker particles kept them within 10 nm of each other and allowed rapid attractive interaction. The unlinked particles either still had a significant barrier during this interval or were too far apart to aggregate within the interval. This was then the role of the linking target molecules; their cations lowered the barrier, so it could be removed by the electric field for an interval in time, and they tethered the two linked nanoparticles so they were driven irreversibly by the attractive vdW force in that interval.

Example 7

Thermodynamic dissociation constants were obtained for the hybridization of different DNA sequences to probe-functionalized gold nanoparticles in a solution-based assay by recording melting curves at numerous target and mismatch concentrations.

Nanoparticles were functionalized with DNA probes shown in Table 1. Typically, after reduction by DTT and purification by spin column, probe P1 was added to 500 μL of a 1 nM nanoparticle solution and incubated at 4° C. for at least twelve hours. Subsequently, 100 mM phosphate buffer was added to the solution to a final concentration of 10 mM. Then 2 M NaCl was added to final concentrations of 0.04, 0.09, 0.15, and 0.30 M in one hour increments. After incubating at 4° C. for another twelve hours, the functionalized particles were washed twice with 500 μL 0.1×PBS using centrifugation speeds of 13,000 rpm for twenty-five to thirty minutes before finally being redispersed in 50 μL 0.1×PBS. The nanoparticle concentration was adjusted to 5 nM by dilution with 0.1×PBS and stored at 4° C. until ready for use. An identical procedure was used for probe P2.

TABLE 1

DNA Sequences

| Name | Label | Sequence (5' → 3') |
|---|---|---|
| Probe 1 | P1 | TGG TTC TCT CCG AAA TAG CTT TAG GGC TA (SEQ ID NO: 5) |
| Probe 2 | P2 | GAA GGG AAG AGG AAG AGG CAG GTG TCC TGT GGT AG (SEQ ID NO: 2) |
| Perfect Target | PT | CT ACC ACA GGA CAC CTG CCT CTT CCT CTT CCC TTC AAAAA TA GCC CTA AAG CTA TTT CGG AGA GAA CCA (SEQ ID NO: 3) |
| Mismatch 2a | MM2a | CT ACC <u>GTA</u> GGA CAC CTG CCT CTT CCT CTT CCC TTC AAAAA TA GCC CTA AAG CTA TTT CGG AG<u>G</u> CAA CCA (SEQ ID NO: 6) |
| Mismatch 2b | MM2b | CT ACC ACA GGA CAC CTG CCT CTT CCT CTT CCC T<u>AT</u> AAAAA <u>AG</u> GCC CTA AAG CTA TTT CGG AGA GAA CCA (SEQ ID NO: 7) |
| Mismatch 4a | MM4a | CTA <u>TTG</u> <u>TAG</u> GAC ACC TGC CTC TTC CTC TTC CCT TC AAAAA TA GCC CTA AAG CTA TTT CGG AG<u>G</u> <u>CGG</u> CCA (SEQ ID NO: 8) |
| Mismatch 4b | MM4b | CT ACC ACA GGA CAC CTG CCT CTT CCT CTT CC<u>T</u> <u>AAT</u> AAAAA <u>AG</u> <u>TTC</u> CTA AAG CTA TTT CGG AGA GAA CCA (SEQ ID NO: 9) |

P1 and P2 possessed dithiol modifiers at the 5' and 3' termini, respectively.
Bold letters indicate bases not part of pairing sequence.
Underlined bases indicate the location of mismatches.

For melting curve experiments, a 1 nM:1 nM mixture of nanoparticles with probes P1 and nanoparticles with probes P2 was used in 1×TAE buffer. Target DNA sequences PT, MM2a, MM2b, MM4a, and MM4b were added to separate solutions at concentrations of 2, 4, 6, and 8 μM and allowed to mix for 48 hours. After mixing, SYBR green I was added to a concentration of 2× and allowed to react for one hour. Melting curves were collected using a Quantagene q225 from Beijing Coolight Technologies. The temperature was raised from 20° C. to 55° C. in increments of 1° C. Each temperature was held for two minutes and fluorescent measurements were recorded every twenty seconds. Five replicates of each target sequence at each concentration were performed.

The melting temperature, $T_M$, located inflection point on the melting curve (FIG. 8A), was determined by taking the derivative of the data numerically using the central finite difference method and then recording the maximum (FIG. 8B). From the melting curves, the melting temperatures were plotted versus the concentrations, C, according to equation 1 where R is the gas constant.

$$\frac{1}{T_M} = \frac{R}{\Delta H_{hyb}} \ln\left(\frac{C}{4}\right) - \frac{\Delta S_{hyb}}{\Delta H_{hyb}} \qquad (1)$$

The enthalpies and entropies of hybridization, $\Delta H_{hyb}$ and $\Delta S_{hyb}$, respectively, were determined from the slope and y-intercept of the lines of best fit in FIG. 8C. The melting temperature of the MM4b sequence was too low to be shown. The free energies of the hybridization reactions, $\Delta G_{hyb}$, were determined at 298 K and then the dissociation constants, $K_D$, were calculated by using Equation 2:

$$\frac{1}{K_D} = e^{-G_{hyb}/RT}. \quad (2)$$

The dissociation constants (Table 2) were on the order of 50 nM and were consistent with previously reported results for similar systems. Lower dissociation constants indicated superior sensitivity because the probes were more readily hybridized with targets at lower concentrations. In this system, however, order of 10 nM dissociation constants were relatively high compared to the relevant samples of interest where the concentrations of DNA or RNA biomarkers are typically on the order of pM or lower. It was also clear from the data in shown in Table 2, that a solution-based equilibrium assay provided poor selectivity. For an equilibrium assay, the ratio of dissociation constants, $K_{D,1}/K_{D,2}$, determined the selectivity of sequence 2 to sequence 1. In Table 2, the selectivity of PT versus MM2a, MM2b, and MM4a was, within error, nonexistent. If both PT and MM2a or MM2b were present in similar concentrations, the assay would not have effectively discriminated between the two.

TABLE 2

Dissociation Constants

| Sequence | $\Delta S_{hyb}$ (kJ/mol) | $\Delta H_{hyb}$ (kJ/mol) | $\Delta G_{hyb}$ (kJ/mol) | $K_D$ (nM) |
|---|---|---|---|---|
| PT | −0.61 ± 0.08 | −223 ± 26 | −42 ± 1 | 42 ± 24 |
| MM2a | −0.72 ± 0.05 | −256 ± 17 | −43 ± 1 | 30 ± 14 |
| MM2b | −0.93 ± 0.09 | −312 ± 31 | −36 ± 2 | 400 ± 250 |
| MM4a | −1.34 ± 0.08 | −443 ± 28 | −42 ± 4 | 42 ± 59 |

Example 8

In order to lower the effective dissociation constant as well as shorten the overall assay time, a microfluidic platform was created which relied on ion concentration polarization by a cation-exchange membrane and aggregation of DNA-linked nanoparticles in gel. In this design, DNA targets linked together nanoparticles functionalized with two different complementary probes into dimers, trimers, and higher multimers. After insertion into the chip (FIG. 7A), electrophoresis drove the sample of gold particles and DNA towards the membrane where electrostatic repulsion prevented the analytes from passing through. Instead, they concentrated at the membrane surface as in FIG. 7B. In the second step, depletion, the field was reversed to separate the unlinked particles from the linked particles possessing captured target molecules. The membrane prevented anions on the reservoir side from passing through to the channel side while anions on the channel side migrated away from the membrane. Furthermore, the electroneutrality constraint prevented cations on the channel side from migrating past the anions despite being driven towards the membrane by the electric field. Consequently, a region depleted of ions formed beneath the membrane and progressed up the channel towards the sample reservoir. The interface between this depletion region and the concentrated ion front created a steep conductivity gradient in which the faster moving monomers, that is, the unlinked particles, separated from the slower moving multimers, the linked particles, based on the difference in their electrophoretic mobilities. The depletion region eventually overtook the particles, and the high electric field induced aggregation of the linked particles. There was clear separation of the monomers and the aggregates (FIG. 1C). The multimers aggregated preferably over the monomers for two reasons. One, the cation condensation around the DNA duplexes lowered the barrier to aggregation. Two, the duplexes tethered multiple particles together thereby keeping two or more particles within range of the attractive van der Waals forces. Subsequently, the aggregates were too large to pass through the pores of the gel and effectively precipitation due to their immobility.

As described in Example 2, this technique achieved a limit of detection down to 10 pM DNA, or about ten million copies. To determine the improvement in the chip-based assay with ion concentration polarization over solution-phase or other assays which possess no preconcentration capabilities, the dissociation constants were examined. In surface-based hybridization assays, the dissociation constant indicates the initial target concentration required to bind fifty percent of the probes. Since it was difficult to accurately quantify the exact amount of probe-target hybridization in the chip assay described herein, an effective dissociation constant, $K_{D,eff}$, was approximated at which fifty percent of our nanoparticles aggregate. From the calibration data, a $K_{D,eff}$ of 1 nM was determined. The $K_{D,eff}$ was lowered even further by extending the enrichment time. For instance, for ten minutes of enrichment this value was lowered to below 500 pM; nearly 100-fold improvement over the equilibrium-based assay which had a dissociation constant of only 50 nM as shown in Table 2. The primary reason for this improvement was the concentration of probes, targets, and cations at the membrane during the enrichment step which drove the hybridization reaction in the forward direction. The aggregation during the depletion step prevented the reverse reaction from occurring and therefore maintained the enrichment effect.

While the enrichment effect suitably enhanced the limit of detection for target molecules, the effect was also pertinent to undesirable nontargets. When the dissociation constant of the nontarget was sufficiently different from that of the target, selectivity was not an issue as demonstrated in Example 2. When the hybridization free energies shared a difference of only a couple kilojoules per mole, such as the sequences in Table 2, then distinguishing targets from mismatches became virtually impossible. The similarity in dissociation constants almost guaranteed mismatches would have reported a false positive signal if they were present within the sample.

Example 9

To overcome the lack of mismatch selectivity, the assay protocol was altered to take advantage of differences in the rates of dehybridization between mismatches and targets as opposed to differences in the magnitudes of the dissociation constants. In short, electric field ramping was used to alter the final amount of hybridized targets or mismatches. The effect of the strength of the electric field during the depletion step on the fraction of aggregation was examined. After initially applying the field at 200 V for one minute, the field was dropped to various voltages for the remainder of the depletion step. As shown in Example 3, the ratio of target intensity to mismatch intensity decreased at higher voltages because there was substantial dehybridization by both targets and mismatches. However, when ramped to a low enough voltage at 125 or 100 V, the particles retained the target DNA while expelling most of the mismatch DNA.

To enhance this further, the effect of changing the amount of time used for the initial depletion potential was explored. The reason for starting at such a high potential was to quickly initiate the onset of the depletion zone and increase the electrical shear force on the particles. As the depletion zone spread away from the membrane, there was a sharp rise in the electric field. This generated a strong electric shearing force which contributed to the dehybridization of targets and mismatches. The longer this strong shear force was active, i.e. during the application of the 200 V, the more dehybridization would occur. However, if active too long, both targets dehybridized nonselectively. When the depletion potential was lowered, dehybridization was enabled but at a slower rate. Furthermore, as the depletion zone grew up the channel, the electric field dropped as the high resistance region increased in length. In addition, the accompanying drop in current indicated Joule heating does not play a significant role in enhancing dehybridization. The current was recorded during the depletion step. The current was relatively low (<1 mA) and continued to fall proportional to the square root of time. Furthermore, the agarose gel and the high surface area to volume ratio of the microchannel provided good heat dissipation. Hence, dehybridization effects were primarily attributed to the electric field.

The amount of time the high electric shear force was applied using the 200V depletion potential before ramping the potential down to 125V for the remainder of the depletion step was varied (FIG. 9, x-axis). For example, for time t=1 min the voltage was held at 200 V for one minute before a step change down to 125 V was made. For example, at time t=0, the depletion voltage began at 125 V with no change for the duration of the depletion step. The fraction of aggregation remaining for the perfectly matched target, the targets with two and four mismatches at the end of the pairing sequence, and the targets with two and four mismatches in the middle of the pairing sequence were compared. The baseline aggregation amount was subtracted in order to accurately compare the selectivity between PT and the other sequences. There was indeed an optimum time to hold the depletion potential at 200 V before ramping to a lower voltage (FIG. 9). This optimum time was dependent on the location as well as the number of mismatches. For instance, there was complete selectivity of PT to all other sequences at 1 min. However, from 1 min to 0.5 min and 0 min, the selectivity ratio decreased for both MM2a and MM2b. This phenomenon was slightly faster for MM2b where the mismatch was in the middle. For MM4a and MM4b, the signal was insignificant until 0 min. Again, the selectivity was slightly better against MM4a although this difference was within error of the confidence intervals. The differences demonstrated here validated the importance of mismatch location in determining selectivity. Previously, mismatches placed within the middle of the pairing sequence significantly increased the difficulty of differentiating the mismatch from the target sequence. Changing the mismatch location from the end of the sequence to the middle of the sequence reduced the selectivity from greater than 75 to only 1.5. As shown in FIG. 9, end mismatches provided inferior selectivity to middle mismatches. However, in this case both middle and end mismatches were distinguished from target. In addition, doubling the number of mismatches from two to four significantly improved the selectivity, and this was true for both the middle and end mismatches. The selectivity was a substantial improvement when compared to the selectivity provided by the ratio of dissociation constants. In the case of an equilibrium assay, when dissociation constants were the determining factors, the PT and MM2a sequences were impossible to distinguish as shown by Table 2. The selectivity for this platform was superior to the values of two to six for previously reported assays which rely on probe-functionalized nanoparticles. Importantly in the assay described herein, an improvement in selectivity beyond the equilibrium value was clearly demonstrated.

Example 10

Although the detection of target DNA benefitted from enrichment at the ion-exchange membrane, the major drawback of this approach was that it could equally enrich undesirable nontarget DNA. While nontargets with a high number of mismatches posed no serious concerns, nontargets with only a few mismatches were virtually indistinguishable from perfectly matched targets. As revealed in Table 2, this was due to the fact that the targets and mismatches had almost identical dissociation constants for hybridization to probe-functionalized nanoparticles. The kinetic solution to this thermodynamic problem was to take advantage of the strong electric field generated during the depletion step to utilize larger differences in dehybridization rates. Reaction coordinate diagrams of FIGS. 10A-10C illustrate this concept. The difference in the thermodynamic Gibbs free energy for hybridization $\Delta\Delta G_{hyb} = \Delta G_{hyb,tar} - \Delta G_{hyb,mis}$ was typically just a few RT for two mismatches giving rise to very little thermodynamic selectivity as shown by equation 3:

$$\frac{K_{D,mis}}{K_{D,tar}} = e^{-\Delta\Delta G_{hyb}/RT}. \tag{3}$$

However, with depletion isotachophoresis, the kinetics of the dehybridization were considered where $\Delta\Delta G^{\ddagger}_{d} = \Delta G^{\ddagger}_{d,\,tar} - \Delta G^{\ddagger}_{d,\,mis}$ was the controlling factor. In the presence of shear, both targets and mismatches dehybridized irreversibly, but they dehybridized at different rates. The shearing force destabilized the duplex thereby raising its energy and reducing the energy barrier, $\Delta G^{\ddagger}_{d}$. For a first order reaction, the relative change in concentration, $C/C_0$, over time, t, with a rate constant, $k_d$, is given by $$\frac{C}{C_0} = e^{-k_d t}. \tag{4}$$

Therefore, given similar initial concentrations, the selectivity will be $$\frac{C_{tar}}{C_{mis}} = e^{-(k_{d,tar} - k_{d,mis})t}. \tag{5}$$

If we substitute in the definitions of the rate constants, equation 5 reduces to $$\frac{C_{tar}}{C_{mis}} = e^{\left[-k_{d,tar}\left(1 - \frac{k_{0,mis}}{k_{0,tar}} e^{-\frac{\Delta\Delta G^{\ddagger}_{d}}{RT}}\right)\right]}, \tag{6}$$

where $k_{0,tar}$ and $k_{0,mis}$ are the pre-exponential factors. To ensure that the target concentration did not decrease appreciably to compromise the sensitivity, irreversible dehybridization was stopped after some time that was not much larger than $1/k_{d,tar}$. At that time, the selectivity was controlled by the double exponential of $\Delta\Delta G^{\ddagger}_d$, which was larger than the single exponential of $\Delta\Delta G_{hyb}$ at equilibrium, even if both quantities were comparable. The difference became exponentially large when the barrier difference was much larger than RT. Therefore, unless the pre-exponential factors for the kinetic constants were very different for the two molecules, due perhaps to entropic effects introduced by the mismatches, the kinetically controlled selectivity was expected to be exponentially (geometrically) better than thermodynamic selectivity for barrier differences much larger than RT. Previously, $\Delta\Delta G^{\ddagger}_d$ was measured for a NanoBioArray chip which also used DNA hybridization to DNA-functionalized gold nanoparticles. That study compared the dehybridization activation free energies for a perfectly matched target and one-base mismatch with twenty-base pairing sequences on 12 nm gold nanoparticles. According to those results, $\Delta\Delta G^{\ddagger}_d$ was −2.7 kJ/mol. From the data in Table 2, a two-base mismatch yielded a $\Delta\Delta G_{hyb}$ of 1 kJ/mol or less if the level of uncertainty was considered. Since $\Delta\Delta G^{\ddagger}_d$ and $\Delta\Delta G_{hyb}$ were both on the order of 1 kJ/mol, the quantities were indeed comparable. Therefore, the kinetic paradigm of dehybridization was expected to facilitate better selectivity than thermodynamic equilibrium.

It is also clear from the experiments described herein that there was a tradeoff between selectivity and signal intensity. This was seen by examining the limits of the target concentration and the selectivity as time went to infinity. From equation 4, the concentration of target approached zero as time goes to infinity. From equation 5, however, since $k_{d,mis}$ was greater than $k_{d,tar}$, the selectivity approached infinity as time went to infinity. While selectivity increases with increasing shear time, a loss in signal intensity due to target dehybridization always accompanied it. In FIG. 3, the selectivity increased with increasing shear time, but the amount of aggregation for target steadily decreased, demonstrating this effect. The goal, therefore, was to maximize the rate at which selectivity approached infinity while simultaneously minimizing the rate at which the target concentration approached zero. Furthermore, this must occur before particle aggregation was induced. To achieve this, cooperative melting was used.

Cooperative melting further enhanced this selectivity by irreversible kinetics allowing retention of a higher concentration of target than by shear alone. As explained above, cooperative melting described how hybridization or dehybridization of one target favorably or unfavorably contributed to further hybridization or dehybridization events. In the experiments described herein, the effect of positive cooperativity on dehybridization was of interest. Positive cooperativity occurs when the surface probe density is between approximately 0.04 and 0.10 oligos per $nm^2$ and when the salt concentration is greater than 0.2 M. Based on previous reports, the surface probe density on the particles was expected to be about 0.08 oligos per $nm^2$. The 1×TAE buffer was 40 mM tris-acetate which easily concentrated more than ten-fold during the enrichment portion of our assay. Therefore, the positive cooperativity region occurred during the initial stages of the depletion step. In this regime, successive dehybridization events were energetically more likely to accompany a reduction in the kinetic energy barrier thereby accelerating the reaction. The reason for acceleration was the association of cations around DNA duplexes. When the targets hybridized to their probes, they required a larger number of cations than either targets or probes alone in order to compensate for the increased charge density. The increased density of cations around the duplexes on the gold nanoparticles provided a stabilizing effect for additional hybridization. Consequently, when targets dehybridized from the nanoparticle probes, they diminished the cation concentration which destabilized the remaining duplexes making dehybridization of the next target energetically more favorable than the previous one.

The positive cooperativity expressed here proved to be highly advantageous for improving the selectivity between targets and mismatches. In essence, cooperativity implied that dehybridization is not one single reaction but rather a series of successive reactions which all possess their own rate constant. If there were N targets bound to each nanoparticle, and the rate constant for each dehybridization would have been $k_N$, then $k_N < k_{N-1} < k_{N-2} \ldots$. In other words, the reaction was self-accelerating. Because mismatches already had a lower rate constant than targets, their dehybridization accelerated at a faster rate than the targets'. In fact, the rate of dehybridization for mismatches could be sped up even more relative to target dehybridization by optimally timing the voltage ramping. After sufficiently accelerating the dehybridization of mismatches, decreasing the electric field at the optimal time allowed retention of the targets by slowing down their dehybridization. Although the rate of mismatch dehybridization also slowed, the initial acceleration provided enough of an impetus to increase the rate well beyond the rate of the target. Therefore the retention of targets was maximized and the number of mismatches was minimized thus increasing the signal intensity while avoiding false positives. This effect was partially obscured by the fact that dehybridization essentially ended once the particles aggregated which was dependent on the growth of the depletion region. The rate of dehybridization and depletion were both dependent on the strength of the electric field, so determining the exact rate of dehybridization remained a complex set of interactions.

Cooperative melting may also explain the discrepancy between this work and our previous work as to the effect of mismatch location. Normally, greater selectivity when mismatches are at the end of the DNA sequence would be expected because duplexes dehybridize through an unzipping mechanism whereby the base pairs break their bonds at one end of the sequence continuing down to the opposite end. The middle mismatches in MM2a were near the particle surface whereas the end mismatches in MM2b were at the opposite end. Near the particle surface was where cooperative melting effected the biggest changes in charge density. It could therefore lower the kinetic barrier to melting for MM2a more so than for MM2a, and this may have accounted for the slightly better selectivity against MM2a. Previously, probe DNA was functionalized on 500 nm silica nanocolloids. It has been pointed out that the behavior of DNA hybridization to surface-functionalized probes on nanoparticles approached that of hybridization to probes on planar surfaces when the diameter of the nanoparticles is above 60 nm. Hence, the cooperative melting effect was likely to be more pronounced for the nanoparticle assay described herein than in the previously reported nanocolloid assembly.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for separating biomolecules, the method comprising:
   a) providing a microfluidic device comprising
      a microchannel having a first end and a second end and containing an electrophoresis matrix,
      an ion permselective membrane in direct contact with the electrophoresis matrix, and
      a first electrode and a second electrode configured to apply an electric field across the ion permselective membrane;
   b) loading a sample containing a plurality of biomolecules, a plurality of first probes and a plurality of second probes into the electrophoresis matrix, wherein each of the first probes comprises a first nanoparticle coupled to a plurality of first binding moieties, and each of the second probes comprises a second nanoparticle coupled to a plurality of second binding moieties, and wherein the first binding moieties and second binding moieties are configured to bind target biomolecules within the plurality of biomolecules;
   c) applying a first electric field that causes the plurality of biomolecules, the plurality of first probes and the plurality of second probes to move through the electrophoresis matrix towards the ion permselective membrane whereupon the plurality of biomolecules, the plurality of first probes and the plurality of second probes become concentrated in the electrophoresis matrix adjacent to the ion permselective membrane, wherein at least some of the target biomolecules bind to one of the plurality of first probes and one of the plurality of second probes to form a plurality of linked nanoparticle multimers comprising at least one first nanoparticle and at least one second nanoparticle; and
   d) applying a second electric field to form an ion depletion front as a result of ion concentration polarization, whereupon the ion depletion front moves away from the ion permselective membrane and whereupon linked nanoparticle multimers at the ion depletion front aggregate and precipitate and whereupon biomolecules, first probes and second probes not contained within a linked nanoparticle multimer move through the electrophoresis matrix away from the ion permselective membrane behind the ion depletion front.

2. The method of claim 1, wherein the plurality of target biomolecules are selected from the group consisting of polynucleotides, polypeptides, proteins or combinations thereof.

3. The method of claim 2, wherein the polynucleotides are comprised of DNA, RNA or a combination thereof.

4. The method of claim 2, wherein the polynucleotides are single stranded, double stranded, or a combination thereof.

5. The method of claim 2, wherein the polynucleotides are comprised of 10 to 1000 nucleotides.

6. The method of claim 1, wherein the plurality of first binding moieties and the plurality of second binding moieties are independently selected from the group consisting of polynucleotides, polypeptides, proteins and small organic molecules.

7. The method of claim 6, wherein the wherein the polynucleotides are single stranded, double stranded, or a combination thereof.

8. The method of claim 6, wherein the polynucleotides are comprised of DNA, RNA or a combination thereof.

9. The method of claim 6, wherein the polynucleotides are comprised of 10 to 1000 nucleotides.

10. The method of claim 1, wherein the plurality of first binding moieties and the plurality of second binding moieties are configured to bind to different locations on the same target biomolecule.

11. The method of claim 1, wherein at least some of the target biomolecules are single stranded polynucleotides comprising a sequence complementary to single stranded polynucleotides of the first binding moiety and single stranded polynucleotides of the second binding moiety.

12. The method of claim 11, wherein the single stranded polynucleotide target biomolecules hybridize to the single stranded polynucleotides of the first binding moiety and single stranded polynucleotides of the second binding moiety to form a double stranded polynucleotide.

13. The method of claim 12, wherein the double stranded polynucleotide comprises less than three base pair mismatches.

14. The method of claim 1, wherein the electrophoretic matrix comprises at least one of gel, paper, fabric and thread.

15. The method of claim 1, wherein the electrophoretic matrix comprises agarose, acrylamide, starch, or a combination thereof.

16. The method of claim 1, wherein the ion permselective membrane is a cation permselective membrane or an anion permselective membrane whereupon the ion permselective membrane contains the same charge as the target biomolecules.

17. The method of claim 1, wherein the first nanoparticle and the second nanoparticle are independently selected from the group consisting of metal nanoparticles, quantum dots, up-conversion nanoparticles or fluorescent dielectric nanoparticles.

18. The method of claim 1, wherein the first nanoparticle and the second nanoparticle are independently selected from metal nanoparticles comprised of gold, silver, copper, aluminum, chromium or an alloy or combination thereof.

19. The method of claim 1, wherein the first nanoparticle and the second nanoparticle are metal nanoparticles comprised of gold.

20. The method of claim 1, wherein the first nanoparticle and the second nanoparticle are between 1 and 500 nm in diameter.

21. The method of claim 1, wherein the first nanoparticle and the second nanoparticle are an identical type of nanoparticle.

22. The method of claim 1, wherein the second electric field is applied in a direction opposite to that of the first electric field.

23. The method of claim 1, wherein the first electric field is applied at a constant voltage.

24. The method of claim 1, wherein the first electric field is applied at between about 5 volts and about 500 volts.

25. The method of claim 1, wherein the second electric field is applied continuously.

26. The method of claim 1, wherein the second electric field is decreased over time.

27. The method of claim 1, wherein the second electric field is decreased linearly.

28. The method of claim 1, wherein the second electric field is decreased stepwise.

29. The method of claim 1, further comprising quantifying the precipitated linked nanoparticle multimers wherein the linked nanoparticle multimers are quantified by measuring the intensity of light absorption or emission of the nanoparticles in comparison to a standard curve.

* * * * *